(12) United States Patent
Crawford et al.

(10) Patent No.: US 11,535,825 B2
(45) Date of Patent: Dec. 27, 2022

(54) ADULT STEM CELL COMPOSITIONS AND METHODS OF IDENTIFICATION AND ISOLATION

(71) Applicant: TACS Bio, Inc., Perrineville, NY (US)

(72) Inventors: Keith D. Crawford, Westwood, MA (US); Baldev Vasir, Boston, MA (US); John Garvey, Londonderry, NH (US)

(73) Assignee: TACS Bio Inc., Perrineville, NY (US)

( * ) Notice: Subject to any disclaimer, the term of this patent is extended or adjusted under 35 U.S.C. 154(b) by 983 days.

(21) Appl. No.: 16/229,942

(22) Filed: Dec. 21, 2018

(65) Prior Publication Data
US 2019/0119632 A1   Apr. 25, 2019
US 2021/0163884 A9   Jun. 3, 2021

Related U.S. Application Data

(63) Continuation of application No. PCT/US2016/048919, filed on Aug. 26, 2016.

(60) Provisional application No. 62/211,307, filed on Aug. 28, 2015.

(51) Int. Cl.
| | |
|---|---|
| C12N 15/85 | (2006.01) |
| C12N 5/074 | (2010.01) |
| C12N 15/79 | (2006.01) |
| G01N 33/53 | (2006.01) |
| G01N 33/569 | (2006.01) |

(52) U.S. Cl.
CPC .......... *C12N 5/0607* (2013.01); *C12N 15/79* (2013.01); *G01N 33/53* (2013.01); *G01N 33/56972* (2013.01); *C12N 2310/20* (2017.05); *C12N 2501/58* (2013.01); *C12N 2501/599* (2013.01); *C12N 2506/00* (2013.01); *G01N 2333/4725* (2013.01); *G01N 2333/70525* (2013.01); *G01N 2333/70596* (2013.01); *G01N 2400/24* (2013.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 8,535,944 B2 * | 9/2013 | Bamdad | C12N 5/0695 435/395 |
| 8,574,567 B2 | 11/2013 | Crawford et al. | |
| 2009/0104158 A1 | 4/2009 | Young et al. | |
| 2009/0186334 A1 | 7/2009 | Young et al. | |
| 2014/0044696 A1 | 2/2014 | Bamdad | |

FOREIGN PATENT DOCUMENTS

| | | |
|---|---|---|
| WO | 2013148334 A1 | 10/2013 |
| WO | 2015017772 A1 | 2/2015 |
| WO | 2015017775 A1 | 2/2015 |

OTHER PUBLICATIONS

Gonzalez, F. Cell Stem Cell. Aug. 7, 2014, vol. 15 (2): 215-226 (Year: 2014).*
Antonov, J., et al., Reliable gene expression measurements from degraded RNA by quantitative real-time PCR depend on short amplicons and a proper normalization. Lab Invest, 2005. 85(8): p. 1040-50.
Atoui, R. and R.C. Chiu, Concise review: immunomodulatory properties of mesenchymal stem cells in cellular transplantation: update, controversies, and unknowns. Stem Cells Transl Med, 2012. 1(3): p. 200-5.
Bentley, S.A., et al., Long-term engraftment failure after marrow ablation and autologous hematopoietic reconstitution: differences between peripheral blood stem cell and bone marrow recipients. Bone Marrow Transplant, 1997. 19(6): p. 557-63.
Chute, J.P., J.R. Ross, and D.P. McDonnell, Minireview: Nuclear receptors, hematopoiesis, and stem cells. Mol Endocrinol, 2010. 24(1): p. 1-10.
Di Campli, C., et al., A human umbilical cord stem cell rescue therapy in a murine model of toxic liver injury. Dig Liver Dis, 2004. 36(9): p. 603-13.
Dominici, M., et al., Minimal criteria for defining multipotent mesenchymal stromal cells. The International Society for Cellular Therapy position statement. Cytotherapy, 2006. 8(4): p. 315-7.
Gratwohl, A. and D. Niederwieser, History of hematopoietic stem cell transplantation: evolution and perspectives. Curr Probl Dermatol, 2012. 43: p. 81-90.
Hikita, S.T., et al., MUC1* mediates the growth of human pluripotent stem cells. PLoS One, 2008. 3(10): p. e3312.
Huang, K., T. Maruyama, and G. Fan, The naive state of human pluripotent stem cells: a synthesis of stem cell and preimplantation embryo transcriptome analyses. Cell Stem Cell, 2014. 15(4): p. 410-5.
Husain, Z., et al., Complex expression of natural killer receptor genes in single natural killer cells. Immunology, 2002. 106(3): p. 373-80.

(Continued)

*Primary Examiner* — Celine X Qian
(74) *Attorney, Agent, or Firm* — Sonia K. Guterman; Preeti T. Arun; Armis Intellectual Property Law, LLC

(57) ABSTRACT

Methods, compositions and cells are provided that identify and isolate a population of adult non-embryonic progenitor cells having multilineage potential, physical diameters of about 2 μm to about 8 μm in size or about 4 μm to about 6 μm, and expressing at least one of the stem cell associated genes among Oct-4, KLF-4, Nanog, Sox-2, Rex-1, GDF-3 or Stella. Methods are also provided that identify and isolate populations, which are subsets or subpopulations of progenitor adult stem cells within the population of the adult stem cells which is a heterogeneous population, the methods including contacting the adult stem cells with a ligand specific for at least one of: CD99, tetraspan, ICAM4, full-length MUC1, and truncated MUC1 receptor, in which a presence of a surface protein on the cells that bind to the ligand identifies the population which is the subset of the differentiated progenitor adult stem cells.

13 Claims, 13 Drawing Sheets
Specification includes a Sequence Listing.

(56) References Cited

OTHER PUBLICATIONS

Insausti, C.L., et al., Isolation and characterization of mesenchymal stem cells from the fat layer on the density gradient separated bone marrow. Stem Cells Dev, 2012. 21(2): p. 260-72.
Keating, A., Mesenchymal stromal cells: new directions. Cell Stem Cell, 2012. 10(6): p. 709-16.
Kucia, M., et al., A population of very small embryonic-like (VSEL) CXCR4(+)SSEA-1 (+)Oct-4+ stem cells identified in adult bone marrow. Leukemia, 2006. 20(5): p. 857-69.
Lindsey, W.B., et al., CD69 expression as an index of T-cell function: assay standardization, validation and use in monitoring immune recovery. Cytotherapy, 2007. 9(2): p. 123-32.
Muraglia, A., R. Cancedda, and R. Quarto, Clonal mesenchymal progenitors from human bone marrow differentiate in vitro according to a hierarchical model. J Cell Sci, 2000. 113 ( Pt 7): p. 1161-6.
Nakagawa, S., et al., Bone marrow stromal cells contribute to synovial cell proliferation in rats with collagen induced arthritis. J Rheumatol, 1996. 23(12): p. 2098-103.
Nauta, A.J. and W.E. Fibbe, Immunomodulatory properties of mesenchymal stromal cells. Blood, 2007. 110(10): p. 3499-506.
Pradines, J., et al., Detection of activity centers in cellular pathways using transcript profiling. J Biopharm Stat, 2004. 14(3): p. 701-21.
Prockop, D.J., Marrow stromal cells as stem cells for nonhematopoietic tissues. Science, 1997. 276(5309): p. 71-4.
Raaijmakers, M.H. and D.T. Scadden, Divided within: heterogeneity within adult stem cell pools. Cell, 2008. 135(6): p. 1006-8.
Ratajczak, M.Z., et al., Very small embryonic-like (VSEL) stem cells: purification from adult organs, characterization, and biological significance. Stem Cell Rev, 2008. 4(2): p. 89-99.
Sakaguchi, Y., et al., Comparison of human stem cells derived from various mesenchymal tissues: superiority of synovium as a cell source. Arthritis Rheum, 2005. 52(8): p. 2521-9.
Sherley, J.L., Accelerating Progress in Regenerative Medicine by Advancing Distributed Stem Cell-based Normal Human Cell Biomanufacturing. Pharmaceutica Analytica Acta, 2014. 5(2): 5 pgs.
Thomson, J.A., et al., Embryonic stem cell lines derived from human blastocysts. Science, 1998. 282(5391): p. 1145-7.
Vasir, B., et al., Fusions of dendritic cells with breast carcinoma stimulate the expansion of regulatory T cells while concomitant exposure to IL-12, CpG oligodeoxynucleotides, and anti-CD3/CD28 promotes the expansion of activated tumor reactive cells. J Immunol, 2008. 181(1): p. 808-21.
Weissman, I.L., Translating stem and progenitor cell biology to the clinic: barriers and opportunities. Science, 2000. 287(5457): p. 1442-6.
Quesenberry, P.J., et al., A New Stem Cell Biology: The Continuum and Microvesicles, Trans Am Clin Climatol Assoc. 2012;123:152-66.
Young, H.E. et al., Adult-derived stem cells, Minerva Biotec 2005, 17: 55-63.
Crawford, K. D. et al. "Isolation and Characterization of Early Lineage Adult Stem Cells from the Synovial Fluid of Osteoarthritis Patients," Jacobs J Regener Med, Sep. 21, 2015 (Sep. 21, 2015), vol. 1, pp. 1-15.
International Search Report and Written Opinion of the International Searching Authority received in PCT/US16/48919, dated Dec. 20, 2016. 10 pgs.

\* cited by examiner

|  | from 1B ↓ 1 | from 1B ↓ 2 | from 1B ↓ 3 |
|---|---|---|---|
| OCT4 (POU5F1) | (-/+) | (-/+) | (-) |
| RUNX2 | (+) | (++) | (++/+++) |
| SOX9 | (-/+) | (+/++) | (+++) |
| REX1 | (+++) | (+++) | (+++) |
| NANOG | (+) | (++) | (+++) |
| CXCR4 | (-) | (-) | (-) |
| SSEA1 | (-) | (-) | (-) |
| CD34 | (-) | (-) | (-) |
| CD73 | (-) | (-) | (-) |
| CD90 | (-) | (-) | (-) |
| CD99 | (+++) | (+++) | (+++) |
| CD133 | (-) | (-) | (-) |
| Class I | (-) | (+) | (+) |
| MUC1 | (+++) | (+++) | (+++) |

Adipocytes

Chondrocytes

Osteocytes

ADULT STEM CELL COMPOSITIONS AND METHODS OF IDENTIFICATION AND ISOLATION

RELATED APPLICATIONS

This application claims the benefit of international application serial number PCT/US2016/048919 filed Aug. 26, 2016 which claims the benefit of U.S. provisional application Ser. No. 62/211,307 tiled Aug. 28, 2015 both entitled, "Adult stem cell compositions and methods of identification and isolation", by inventors Keith D. Crawford, Baldev Vasir, and John Garvey, each of which is incorporated by reference herein in its entirety.

TECHNICAL FIELD

The invention relates to the field of adult stem cells and identification and isolation of adult stem cell populations, as well as tissue regeneration and regenerative medicine applications using such cell populations.

BACKGROUND

Stem cells have the remarkable capacity to self-renew, differentiate into multiple cell lineages, and reconstitute tissue in vivo [Weissman, I. L., Science, 2000. 287(5457): p. 1442-6]. Embryonic stem cells (ESCs), a pluripotent cell type, are established from early embryonic cells and possess the ability to differentiate into all three germ layers [Martin, G. R., Proc Natl Acad Sci USA, 1981. 78(12): p. 7634-8; Evans, M. J. et al. Nature, 1981. 292(5819): p. 154-6; Thomson, J. A., et al. Science, 1998. 282(5391): p. 1145-7; Thomson, J. A., et al. Proc Natl Acad Sci USA, 1995. 92(17): p. 7844-8]. In contrast, adult stem cells (ASCs) are found in the developing fetus with the formation of renewing tissues and postnatally [Keating, A. Cell Stem Cell, 2012. 10(6): p. 709-16; Keating, A. Curr Opin Hematol, 2006. 13(6): p. 419-25]. Hematopoietic stem cells (HSCs), one of the most characterized types of ASCs, have been studied for over 50 years and are known progenitors of various blood cell types [Huang, X., et al. Cell Death Differ, 2007. 14(11): p. 1851-9; Chute, J. P., et al. Mol Endocrinol, 2010. 24(1): p. 1-10; Zon, L. I., Nature, 2008. 453(7193): p. 306-13]. HSCs have been used clinically to reconstitute bone marrow (BM) cells destroyed by BM ablation therapy for cancer [Bentley, S. A., et al. Bone Marrow Transplant, 1997. 19(6): p. 557-63; Greinix, H. T., et al. Bone Marrow Transplant, 1994. 14(2): p. 307-13]. There is also a heterogeneous population of non-hematopoietic stem cells in the BM. In particular, mesenchymal stem/progenitor cells (MSCs) are also thought to originate from the BM and comprise 0.01-0.001% of nucleated BM cells [Sakaguchi, Y., et al. Arthritis Rheum, 2005. 52(8): p. 2521-9]. MSCs are found in the peripheral blood, umbilical cord blood, adipose tissue, skeletal muscle, liver, lungs, synovium, dental pulp, apical papilla, amniotic fluid, and fetal blood.

Because MSCs are found in extremely low numbers in the BM, sustained ex vivo culture on tissue culture plastic is required to generate sufficient cell numbers for phenotypic characterization. MSCs most commonly express surface markers such as CD29, CD44, CD49a-f, CD51, CD73, CD105, CD106. CD166, and Stro1 and lack expression of hematopoietic lineage markers such as CD11b, CD14, and CD45 [Dominici, M., et al. Cytotherapy, 2006. 8(4): p. 315-7]. MSCs are multipotent ASCs capable of differentiating into various mesodermal tissues, such as adipose, cartilage, and bone [Dominici et al. supra; Quesenberry, P. J., et al. Ann N Y Acad Sci, 2007. 1106: p. 20-9; Quesenberry, P. J., et al. Trans Am Clin Climatol Assoc. 2012:123:152-66]. Other groups have reported that MSCs are capable of differentiating into ectodermal and endodermal tissues, such as lung, skin, pancreas, and liver tissue [Prockop, D. J. Mol Ther, 2009. 17(6): p. 939-46; Antonov, J., et al. Lab Invest, 2005. 85(8): p. 1040-50]. A precursor cell of size less than one micron has been described in Young et al., isolated from adult skeletal muscle and testis which is capable of developing into all somatic tissue and spermatogonia, and has been designed as a gblastomere-like stem cell [Young et al., Minerva Biotec 205, 17: 55-63; Young et al., U.S. patent application Ser. No. 11/574,622 filed Aug. 24, 2005 and Ser. No. 12/280,833 filed Jan. 26, 2009]. These however are quiescent and fail to replicate in vivo. There is a need for adult non-embryonic stem cells for repair of tissues and genetic defects.

SUMMARY

An aspect of the invention provides a method for identifying a population of progenitor cells, the method including:
obtaining from a sample tissue or fluid, a population of somatic cells including subpopulations of progenitor cells,
enriching at least one progenitor cell subpopulation relative to the somatic cells, said enriching further including selecting cell subpopulations in which the cells have physical diameters of about 4 µm to about 6 µm in size,
assaying the enriched progenitor cell subpopulation for expression of one or more of stem cell associated genes Oct-4, KLF-4, Nanog, Sox-2, Rex-1, GDF-3 or Stella, whereby statistically significant expression of stem cell associated genes is predictive of a subpopulation having multilineage potential, and
identifying the subpopulation as a progenitor cell population based on gene expression.

According to various embodiments of this method the tissue or fluid is of biological origin, for example, human, or from another mammal or warm blooded animal, and the cell size is about 2 µm to about 8 µm, or about 2 µm to about 6 µm, or about 4 µm to about 8 µm, or about 4 µm, about 5 µm, or about 6 µm, and may even range to about 8 µm. The obtaining can be made remotely from the remainder of the method, for example, the biological fluid may be obtained at a hospital, or may be part of a blood bank, and the remainder of the method is performed under sterile conditions in a cell biology laboratory setting.

The population so identified is envisioned as containing various subpopulations, accordingly the method in further embodiments includes identifying a cell surface polypeptide or peptidoglycan on cells within a subpopulation of the progenitor cells thereby identifying the subpopulation as having multilineage potential.

The method according to various embodiments further includes detecting on cell surface of the progenitor cell subpopulation, the presence of one or more surface antigens including CD99, tetraspan, ICAM, a Mucin, such as MUC1 and its isoforms. CD11b, CD13, CD14, CD29, CD34, CD44, CD45, CD49a, CD49b, CD49c, CD49d, CD49e, CD49f, CD51, CD73, CD90, CD105, CD106, CD166, Oct-4, KLF-4, MHC class I, MHC class II, and StrO1.

In certain embodiments, the MUC1 isoform has a truncated MUC1 receptor region, and detection of this isoform further identifies the progenitor cell subpopulation as having multilineage potential. For example, the truncated MUC1 receptor is MUC1 growth Factor Receptor (MGFR) having an amino acid sequence of a primary sequence of the MUC1 Growth Factor Receptor (PSMGFR). In various alternative embodiments, the cell surface antigen is a member of ICAM family of molecules. For example, the ICAM is ICAM 4 or ICAM5. In particular embodiments, identifying the cell surface polypeptide or peptidoglycan is determined by proteomic analysis.

The method in various embodiments further includes obtaining and correlating tissue-specific gene expression information, microRNA analyses and/or proteomic information to determine a tissue differentiation potential for the subpopulation. The inventors have determined that the cells so identified are pluripotent, such that these cells include a plurality of subpopulations, for example, a first subpopulation, a second subpopulation, etc., each of which is identified by these criteria and each having unique useful differentiation potentials characteristic of each subpopulation. Accordingly, the method further includes expanding the progenitor cell subpopulation and determining tissue differentiation potential. From each subpopulation so identified and isolated, the method further includes inducing lineage differentiation during expansion and determining tissue differentiation potential. For example, a mesodermal lineage differentiation is induced. Alternatively, an endodermal lineage differentiation is induced. Alternatively, an ectodermal lineage differentiation is induced. Each of these lineages is multipotent, capable of further differentiating into a variety of tissues characteristic of the specific germ line.

An aspect of the invention provides a population of isolated human progenitor cells, including: a plurality of cells having diameters ranging from about 4 μm to about 6 μm, which express one or more of stem cell associated genes Oct-4, KLF-4, Nanog, Sox-2, Rex-1, GDF-3 or Stella, and are CD99+ or a MUC-1+ isoform, but do not detectably express surface antigens CD34, CD44, CD73, CD90, CXCR4 or SSEA-4. The population of isolated human progenitor cells in a general embodiment express one or more of a tetraspan, an ICAM, CD13, CD45, CD105, CD133, MHC class I or MHC class II. Several sub-populations are characterized, which are described alternatively herein as a first, a second, a third subpopulation, etc. For example: the population of isolated expanded human progenitor cells express at least one of Oct-4, KLF-4, Nanog, Sox-2, Rex-1, GDF-3, and Stella, and is CD13+ but does not detectibly express, CD34, CD45, CD90, and MHC class I. For another example, the population of isolated expanded human progenitor cells express at least one of Oct-4, KLF-4, Nanog, Sox-2, Rex-1, GDF-3, and Stella, and do not detectibly express CD13, CD34, CD45, CD90, and is MHC class I+. For yet another example: the population of isolated expanded human progenitor cells according to claim 15, wherein the cells express at least one of Oct-4, KLF-4, Nanog, Sox-2, Rex-1, GDF-3, and Stella, and do not detectibly express CD13, CD34, CD45, CD90, but are MHC class I+ and CD105+. For yet another example, the population of isolated expanded human progenitor cells express at least one of Oct-4, KLF-4, Nanog, Sox-2, Rex-1, GDF-3, and Stella, and do not detectibly express CD13, CD34, CD45, CD90, is MHC class I−, and CD105+.

Accordingly, an embodiment of the invention provides an induced population of isolated and expanded human progenitor cells, which have the properties above as previously described, with mesodermal lineage differentiation potential. Alternatively, an embodiment of the invention provides an induced population of isolated and expanded human progenitor cells with endodermal lineage differentiation potential, or alternatively provides an induced population of isolated and expanded human progenitor cells with ectodermal lineage differentiation potential. It is within the scope of the embodiments of the invention herein the cells are isolated by methods provided herein or are both isolated and are expanded by methods provided herein.

In a further embodiment, the isolated human adult stem cells carry a recombinant polynucleotide encoding a transgene. For example, the transgene further includes at least one of a CRISPR nucleotide sequence and a gene encoding a Cas protein. Alternatively, the stem cells carry a recombinant polynucleotide encoding a transgene, which is a therapeutic high value protein such as a growth factor, for example, an osteogenic growth factor, a hemopoietic growth factor, or a transgene that supplies a protein, which might otherwise be defective, such as a normal hemoglobin or other product of a mutation.

In general, the isolated human adult stem cells are characterized in having a particular size or size range, for example, at least about 2 μm to about 8 μm; about 3 μm to about 7 μm; about 4 μm to about 8 μm; about 4 μm to 7 μm; and on average about 5.9 μm in diameter. For example, the isolated human adult stem cells have a mean diameter of about 5.9 μm. In various embodiments, the isolated human adult stem cells have a diameter greater than about 6 μm and are MHC class I+.

An aspect of the invention provides a method of identifying and isolating a cell population which is a subset of adult stem cells within a heterogeneous pool of the adult stem cells, the method including contacting the adult stem cells with a ligand specific for at least one of: CD99, tetraspan, ICAM4, full-length MUC1, and truncated MUC1 receptor, such that the presence of the ligand identifies the population which is the subset of ELA cells.

An aspect of the invention provides a method of identifying and isolating a population which is a subset of primitive adult stem cells having pluripotency properties within a heterogeneous pool of adult stem cells the method including, contacting the adult stem cells with a ligand specific for at least one of: CD99, tetraspan, ICAM4, full-length MUC1 and or truncated MUC1 receptor, such that a presence of the ligand identifies the population which is the subset of the primitive adult stem cells having the pluripotency properties.

An aspect of the invention provides a method of identifying and isolating a population which is a subset of undifferentiated progenitor adult stem cells within a heterogeneous pool of the adult stem cells, the method including, contacting the adult stem cells with a ligand specific for at least one of: CD99, tetraspan, ICAM4, full-length MUC1 and or truncated MUC1 receptor, wherein the presence of the ligand identifies the population which is the subset of the undifferentiated progenitor adult stem cells.

An aspect of the invention provides a method of identifying and isolating a population which is a subset of differentiated progenitor adult stem cells within a heterogeneous pool of the adult stem cells, the method including, contacting the adult stem cells with a ligand specific for at least one of: CD99, tetraspan, ICAM4, full-length MUC1, and truncated MUC1 receptor, wherein a presence of the ligand identifies the population which is the subset of the differentiated progenitor adult stem cells.

An aspect of the invention provides a method for identifying a population of progenitor cells, the method including:

obtaining from a sample tissue or fluid, a population of somatic cells including subpopulations of progenitor cells, enriching at least one progenitor cell subpopulation relative to the somatic cells, said enriching further including selecting cell subpopulations having physical diameters of about 2 µm to about 8 µm in size, assaying the enriched progenitor cell subpopulation for expression of one or more of stem cell associated genes Oct-4, KLF-4, Nanog, Sox-2, Rex-1, GDF-3 or Stella, whereby statistically significant expression of stem cell associated genes is predictive of a subpopulation having multilineage potential, and identifying the subpopulation as a progenitor cell population based on gene expression.

In one aspect, the present invention is directed to a method of identifying and isolating pluripotent primitive cells from a heterogeneous population of ELA stem cells or ELA-like cells or ELA-related cells, including: obtaining a heterogeneous population of ELA cells; contacting the population with at least one of: an antibody, aptimer, or compounds (small molecule) that bind to MUC1, NM23 or NME7; and identifying and isolating the cells bound to these compounds. For example, an antibody that binds to 35 amino acids at the N-terminal of the PSMGFR peptide. In an embodiment of the invention, the ELA cell sample is obtained from a subject having osteoarthritis (OA). Alternatively, ELA cell samples are obtained from other tissues such as blood, fat, amniotic fluid, or placenta. Alternatively, the ELA cell sample is obtained from umbilical cord blood or umbilical cord tissue.

In another aspect, the present invention is directed to a method for enriching a heterogeneous population of ELA stem cells, including: obtaining a sample of a heterogeneous population of ELA cells; contacting the sample with an antibody that binds to MUC1, such that the antibody selectively binds to pluripotent ELA cells, and enriching the cells bound with the antibody. In an embodiment of the invention, the antibody is bound to the 35 amino acids at the N-terminal of the PSMGFR peptide.

In yet another aspect, the present invention is directed to a method for enriching from a heterogeneous population of ELA stem cells, including: obtaining a sample of a heterogeneous population of ELA cells; contacting the sample with an aptimer that binds to MUC1, such that the aptimer selectively binds to pluripotent ELA cells, and enriching the cells bound with the aptimer. In an embodiment of the invention, the aptimer is bound to the 35 amino acids at the N-terminal of the PSMGFR peptide.

In yet another aspect, the present invention is directed to a method for enriching for from a heterogeneous population of ELA stem cells, including: obtaining a sample of a heterogeneous population of ELA cells; contacting the sample with a compound (small molecule) that binds to MUC1, such that the compound (small molecule) selectively binds to pluripotent ELA cells, and enriching for the cells bound with the compound (small molecule). In an embodiment of the invention, the compound is bound to the 35 amino acids at the N-terminal of the PSMGFR peptide.

In yet another aspect, the present invention is directed to a method for generating biologically useful ELA cell progenitor cells including: obtaining a sample of a heterogenous population of ELA cells; contacting said ELA cell sample with an antibody, aptimer, or other MUC1 binding compound, such that the compound selectively binds to the pluripotent ELA cell subset; and isolating the cells bound to the compound. In an embodiment of the invention, the method further includes expanding the isolated cells bound to the compound to obtain expanded cells. In an embodiment of the invention, the method includes inducing the isolated cells bound to the compound in a less mature state before expanding the isolated cells. In an embodiment of the invention, the method includes inducing differentiation of the expanded cells. In an embodiment of the invention, the isolated cells or expanded isolated cells are banked for future use.

An aspect of the present invention provides a population of isolated human progenitor cells obtained according to methods described herein.

BRIEF DESCRIPTION OF DRAWINGS

FIG. 1A is a representative forward- and side-scatter profiles of mononuclear cells isolated from the SF of an OA patient indicating the location of a small cell population in relation to other cell types.

FIG. 1B is a forward- and side-scatter profile of a gated small population of cells depicting a heterogeneous population with a varied cell size and scatter profile.

FIG. 1C is a viability and cell-size determination of a gated small cell population using the Roche CASY Cell Counter and Analyzer System.

FIG. 1D is a table showing the expression of pluripotent intracellular and surface markers determined by FACS analysis of a gated population of small cells in Group 1, Group 2, and Group 3.

FIG. 1E is a photograph of RT-PCR analysis of pluripotency marker expression in a small cell population isolated from three separate samples of SF, with NTERA-2 cells (a stem cell line) as a positive control. Primers are specific for transcripts from the respective endogenous locus. GAPDH was used as a loading and internal control.

FIG. 2A is a bar graph depicting growth of ELA cells from two separate donors cultured in standard culture media or chemically defined (CD) culture media with or without 1% fetal bovine serum (FBS).

FIG. 2B are phase micrographs demonstrating pattern and density of ELA cell growth at two different magnifications.

FIG. 2C are phase micrographs exhibiting the pattern and density of ELA cell growth at day 1, 4, and 7 in CD media supplemented with 1% FBS from three separate donors.

FIG. 2D is a bar graph of total ELA cell counts from three separate donors cultured in CD media with 1% FBS at different passage numbers. Numbers in parenthesis represent population doubling time during labeled passage growth period.

FIG. 3A is a micrograph showing Adipogenic differentiation, which was indicated by accumulation of neutral lipid vacuoles that stained with Oil Red O.

FIG. 3B is a micrograph showing Chondrogenic differentiation, which was assayed with Alcain Blue that labelled the acid mucopolysaccharides and glycosaminoglycans of cartilage. Diffuse blue staining was observed throughout the slide.

FIG. 3C is a micrograph showing the osteogenic differentiation, which was assayed with BCIP/NBT, a substrate that turns purple in the presence of alkaline phosphatase. Uninduced cells were used as negative controls in the differentiation experiments. Total RNA was extracted from these differentiated cells, and cDNA derived from mRNA was amplified based on the global PCR protocol described in examples herein.

FIG. 3D, FIG. 3E and FIG. 3F are bar graphs showing Real-time RT-PCR analysis of selected specific genes expressed in differentiated ELA cells. The expression of genes was compared to the expression of beta-actin as an internal control and the values expressed as ΔCT. Negative bars indicate a decrease in expression of that particular gene. FIG. 3D shows ELA cells differentiated into adipocytes. FIG. 3E shows ELA cells differentiated into chondrocytes. FIG. 3F shows ELA cells differentiated into osteocytes.

FIG. 4A is a dendrogram comparing gene expression in primary ELA cells, BM-derived MSCs, CD105+ MSCs, and CD133+ MSCs.

FIG. 4B is a dendrogram of a hierarchical cluster analysis comparing genes expressed in expanded ELA cells compared to MSC gene data sets available from the NIH gene Expression Omnibus in addition to those generated in examples herein.

FIG. 4C are volcano plots comparing specific genes upregulated in primary ELA cells and expanded ELA cells (upper left), BM-derived MSCs (upper right), CD105+ MSCs (bottom left), and CD133+ MSCs. Genes expressed above the broken red line represent genes specific to primary ELA cells on the left and genes specific to MSCs on the right.

FIG. 4D is a Venn diagram comparing upregulated genes in expanded ELA cells. BM-derived MSCs, CD105+ MSCs, and CD133+ MSCs.

FIG. 4E are Venn diagrams depicting the percentage of genes expressed in expanded ELA cells that overlap with other categories of stem cells, utilizing published gene datasets available from the NIH Gene Expression Omnibus.

FIG. 5A is a bar graph showing that stimulation of allo-reactive T cells was determined by co-culturing irradiated and non-irradiated ELA cells with freshly isolated peripheral blood mononuclear cells (PBMCs) at ratios of 1:10, 1:100 and 1:1000 in triplicate for 5 d. PBMCs were isolated from healthy donors, and previously expanded ELA cells were irradiated. To determine the proliferation of allo-reactive T cells, cultures were pulsed with 3[H]-Thymidine (1 μCi/well) 18 h prior to harvesting. Bar graphs represent the mean±SEM of 5 replicates.

FIG. 5B is a bar graph showing the effectiveness of cryopreserved ELA cells to stimulate allo-reactive T cell proliferation was determined as in FIG. 5A. Bar graphs represent the mean of 3 separate replicates ±SEM.

FIG. 5C is a bar graph showing that the immunosuppressive properties were further investigated by culturing ELA cells or MSCs with 5-6-carboxyfluorescein diacetate succinidyl ester (CFSE)-labeled allo-reactive T cells at various ratios in triplicate. After five day culture, T cells were analyzed by flow cytometry to determine CFSE fluorescence. T cell suppression was expressed as the Proliferation Index.

FIG. 5D is a bar graph showing that the immunosuppressive effectiveness of each ELA cell passage was determined by using different passage numbers of cells co-cultured with CFSE-labeled T cells.

FIG. 5E is a bivariate dot plot analysis of a representative experiment of expanded ELA cell/freshly isolated PBMC co-culture (1:10 ratio) to determine the expression of CD25 on CD4+ and CD8+ T cells and the expression of CD69 or PD1 on CD3+ T cells (* p<0.001: ** p<0.01 as compared with MSCs).

FIG. 5F is a Bar graph which represent the mean of 3 separate replicates ±SEM (* p<0.001 as compared with PBMCs alone).

FIG. 5G is a line graph showing that the inhibitory effect of ELA cells on NK cell cytotoxicity was demonstrated by co-culturing NK cells with or without ELA cells prior to incubation with target cells at various ratios.

DETAILED DESCRIPTION

Figure 1A:
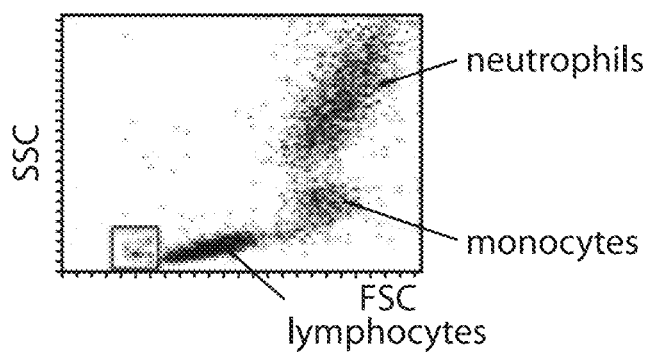
FIG. 1A, FIG. 1B, FIG. 1C, FIG. 1D and FIG. 1E are scatter graphs, photographs, and tables showing the identification of early lineage adult (ELA) stem cells in the synovial fluid (SF) of patients with osteoarthritis (OA).

Adult stem cells (ASCs), which possess the ability to self-renew and regenerate tissue, are of significant value for the development of cellular therapies, tissue engineering tools, and drug screening models. Conventional protocols for ASC enrichment generate a small number of cells that do not represent the total ASC population of tissues. By avoiding prior conventional methodologies, a heterogeneous subpopulation of ASCs termed early lineage adult (ELA) stem cells was identified, Crawford et al., U.S. Pat. No. 8,574,567 issued Nov. 5, 2013 which is incorporated herein by reference in its entirety.

Provided herein are subpopulations of multipotent progenitor cells and ASCs, within a heterogeneous pool, the cells having a size approximately of 4-6 μm in diameter, derived from the synovial fluid of osteoarthritic patients which is a well-studied source of ELA cells. "ELA" as used herein in is defined as cells lacking the classical mesenchymal ASC markers CD73, CD90, and CD105. RT-PCR analysis of the ELA cells indicate expression of pluripotency genes such as NANOG, OCT4, REX1, KLF4, STELLA, and SOX, as further described in Crawford et al., U.S. Pat. No. 8,574,567 issued Nov. 5, 2013; Crawford et al., U.S. patent application Ser. No. 13/430,998 filed Mar. 27, 2012; Crawford et al., International patent application serial number PCT/US13/32255 filed Mar. 15, 2013; Crawford et al., International patent application serial number PCT/US14/49395 filed Aug. 1, 2014; Crawford et al., International patent application serial number PCT/US14/49401 filed Aug. 1, 2014; Crawford et al., U.S. application Ser. No. 14/453,937 filed Aug. 7, 2014 and Crawford et al., U.S. application Ser. No. 14/497,690 filed Sep. 26, 2014 each of these patents and applications are hereby incorporated herein by reference in their entireties. "ELA" as used herein includes also a heterogeneous pools of cells that are further isolated, the cells being approximately 4-6 μm in diameter, or about 2 μm to 8 μm as described in examples herein, which include smaller diameter populations with greater potential for early lineage properties.

As cultured in adipogenic, chondrogenic, or osteogenic differentiation media, ELA cells are shown herein to be capable under appropriate culture media to be differentiated into fat, cartilage, and bone tissue, respectively. Furthermore, ELA cells were observed to have strong in vitro immunomodulatory properties as these cells inhibit T cell proliferation, inducing CD4+/CD25+ regulatory T cells, and inhibiting natural killer cell activity. Collectively, these results indicate that ASC subpopulations of ELA are useful for cell-based regenerative therapies and the treatment of systemic diseases, particularly with immunological etiologies.

Quantitative PCR analysis of ELA cells were used to show unique molecular signatures consisting of both tissue-specific and remnant mRNA in the differentiated tissues, indicating a continuum of mRNA expression. Furthermore, the ELA cell sub-populations were found to share unique gene sets with embryonic stem cells, mesenchymal stem cells, and induced pluripotent stem cells. Some of these genes are known to be unique to neuronal, cardiac, pancreatic, and hepatic progenitor cells, and others, such as mucins, ICAM, and tetraspans, have tissue-specific cell functions. These analyses and the specific markers provide methods of predicting and monitoring tissue lineage differentiation potentials, in culture or in situ, or modeling microenvironment effects. Other applications of the ELA cells involve cell sorting, cell identification or targeting, and use in the manufacture and selection of cell-lines.

Many groups have studied the human bone marrow stromal cells (MSC) and demonstrated phenotypic and functional heterogeneity [Ratajczak et al., supra; Orkin, S. H. et al., Nat Immunol, 2002. 3(4): p. 323-8; Raaijnakers, M. H. et al. Cell, 2008. 135(6): p. 1006-8]. With use stem cell nomenclature has changed from initially representing a heterogeneous population of marrow cells to a single group of adult stem cells, namely mesenchymal stem cells. During early bone marrow studies, populations of cells were discovered with self-renewing traits and referred to as stem cells. These stem cells were later subdivided into hematopoietic and nonhematopoietic subpopulations [Friedenstein, A. J. et al. J Embryol Exp Morphol, 1966. 16(3): p. 381-90; Friedenstein, A. J. et al. Transplantation, 1968. 6(2): p. 2521-9; Owen, M. et al. Ciba Found Symp, 1988. 136: p. 42-60]. The hematopoietic stem cells, one of earliest and well-characterized bone marrow stromal stem cell, were used for successful cellular therapies. Presently, over 50,000 hematopoietic stem cell transplants have been performed worldwide [Gratwohl, A. et al. Curr Probl Dermatol, 2012. 43: p. 81-90]. MSCs were originally designated by their ability to bind a reference antibody (see, U.S. Pat. No. 5,486,359) and were commonly characterized by ability to differentiate into tissues of mesodermal origin [Prockop. D. J. Science, 1997. 276(5309): p. 71-4].

However, not all marrow stromal cells are capable of differentiating into various tissues, nor are these cells phenotypically and functionally identical [Di Campli, C., et al. Dig Liver Dis, 2004. 36(9): p. 603-13; Orlic, D., et al. Nature, 2001. 410(6829): p. 701-5; Lagasse, E., et al. Nat Med, 2000. 6(11): p. 1229-34]. The majority of our understanding of marrow stromal was derived from studies involving MSC, leading many to believe the existence of one category of adult stem cells having a hierarchical relationship with other adult stem cells [Muraglia, A. et al. J Cell Sci, 2000. 113 (Pt 7): p. 1161-6]. To the contrary, it is here envisioned that within the bone marrow stroma there exists a large and heterogeneous population of adult stem cells. Specific recognized subpopulations include those such as, mesenchymal precursor cell (MPC), marrow-isolated adult multilineage inducible (MIAMI) cells, multipotent adult progenitor cells, multipotent adult progenitor cells (MAPCs), very small embryonic-like stem cell (VSEL). These are largely homogeneous populations relative to the total and consequently poorly represented and difficult to isolate.

The examples herein describe isolated sub-populations of adult stem cells, obtained from ELA cells, which contribute to the heterogeneity of the marrow stromal cell population. ELA used in this study thus represents a $MUC1^+/CD99^+/CD235a^-/MHC$ class $I^-$ subpopulation derived from the synovial fluid of osteoarthritic patients. The properties of these ELA cells, was determined by protein and mRNA analysis for pluripotency genes and proteins, examples of which are the OCT4 (embryonic form), REX1, and NANOG.

The method of isolation described in examples herein is less cumbersome than methods required for the enrichment of stem cells from other tissues, because of the absence RBCs in synovial fluid. Accurate measurements of ELA cell size, volume, and viability were performed with instrumentation that incorporated the Coulter principle, which states that particles pulled through an orifice, concurrent with an electric current, produce a change in impedance that is proportional to the volume of the particle traversing the orifice. This methodology provides accurate measurements of cell size, and distinguishes between cellular debris and viable cells. The ELA population size measurement was observed to range between approximately 4-6 μm, in contrast to RBCs, which are 6-8 μm. Of note, the majority of stem cells studies have utilized forward and side scatter perimeters on the flow cytometric, which excludes events less than 6 μm in size. This gating strategy is why the original ELA cell subpopulation was described as 6 μm in size or greater, and why it is here envisioned that smaller cells have been overlooked.

The ELA cell population provided here is phenotypically and morphologically distinct from other stem cell populations. It is similar in size to the VSEL cell, which expresses OCT-4 and possesses the capacity to differentiate into three germ layers [Kucia, M., et al. Leukemia, 2006. 20(5): p. 857-69]. A precursor cell of size less than one micron has been described in Young et al., isolated from adult skeletal muscle and testis (Young et al., Minerva Biotec 205, 17: 55-63; Young et al., U.S. patent application Ser. No. 11/574, 622 filed Aug. 24, 2005 and Ser. No. 12/280,833 filed Jan. 26, 2009 and Ser. No. 12/280,833 filed Jan. 26, 2009). It is capable of developing into all somatic tissue and spermatogonia, and has been designed as a gblastomere-like stem cell.

The ELA cell population does not express CXCR4, SSEA-4, CD34, and CD133, which are additional markers used to identify VSEL cell populations [Kucia et al. supra]. The human ELA cell population is functionally distinct from the VSEL, as evidenced that ELA cells proliferate in the absence of feeder cells. Taken together, these data indicate that the ELA cell population is distinct from the VSEL population. Furthermore, the data described in Examples herein distinguish the ELA cell population from the VSEL cell population and distinguish ELA cells from other categories of ASCs. These data raise the question of whether the ELA cell population represents a heterogeneous population of primitive stem or progenitor cells.

In addition to the expression of pluripotency gene transcripts encoding for NANOG, OCT4, Rex-2, and DPPA3, the ELA sub-populations characterized herein express high levels of MUC1. Moreover, transcriptome assays described herein show the high expression of mucins. Recently studies pertaining to human pluripotent stem cells have shown a relationship between MUC1 and the state of differentiation of ESCs [Hikita, S. T., et al. PLoS One, 2008. 3(10): p. e3312]. It is a recognized need herein, which is addressed by the methods to effectively distinguish between the least differentiated form of ASCs, in particular the ELA cell population, in any heterogeneous pool of ASCs. Use of cell surface proteins such as MUC1 to distinguish between primitive undifferentiated ASCs, including ELA cells, and those ASCs in an intermediate or later stage of tissue type differentiation [Huang, K., et al. Cell Stem Cell, 2014. 15(4): p. 410-5]. Collectively, these data indicate that the ELA cell populations isolated, identified and characterized in examples herein represent primitive forms of ASC, making these cell types useful for successful stem cell based treatment.

The cell surface receptor MUC 1 is present at apical borders of healthy epithelium of the cell and is aberrantly expressed (spread over the entire cell surface) in stem cells and progenitor cells. MUC1 protein can be cleaved or "shed" from the cell surface. The MUC1 ectodomain consists of distinct regions: the tandem repeats; an interchain binding region that self-aggregates; and the portion of the receptor that remains attached to the cell surface following proteolysis, called MUC1 growth factor receptor (MGFR). The portion of the MUC1 receptor that remains attached to the cell surface after cleavage, consisting primarily of PSMGFR is a growth factor receptor that mediates the growth of stem or progenitor cells in vitro.

While classical ELA cells are CD99+ and MUC-1+, we note these markers are useful in connection with the pluripotency gene transcript data to identify additional CD99+ and/or MUC-I+ subpopulations of progenitor cells (i.e., CD13+, and/or CD105+ and/or MHC class I+ subpopulations), preferable approximately 4-6 µm or larger in diameter. See, for example FIG. 1B and FIG. 1D. These subpopulations can be assayed for tissue lineage potential as described for ELA cells. For example, one ASC subpopulation expresses at least one of Oct-4, KLF-4, Nanog, Sox-2, Rex-1, GDF-3, and Stella, and is CD13+ but does not detectibly express, CD34, CD45, CD90, and MHC class I. Another subpopulation expresses at least one of Oct-4, KLF-4, Nanog, Sox-2, Rex-1, GDF-3, and Stella, and does not detectibly express CD13, CD34, CD45, CD90, but is MHC class I+. Yet another subpopulation expresses at least one of Oct-4, KLF-4, Nanog, Sox-2, Rex-1, GDF-3, and Stella, and does not detectibly express CD13, CD34, CD45, CD90, but is MHC class I+ and CD 105+. Yet another subpopulation expresses at least one of Oct-4, KLF-4, Nanog, Sox-2, Rex-1, GDF-3, and Stella, and this subpopulation does not detectibly express CD13, CD34, CD45, CD90, is MHC class I-, but is CD105+. These protein expression patterns exemplify characteristics of subpopulations distinct from the classical ELA cells and sharing the same early lineage potentials. Thus, in addition to physiological size and positive expression of CD99 and/or MUC-1, expression of stem cell genes, either high levels or multiple genes, or both, indicate early lineage potential. Such features provide methods to identify and sort progenitor cell populations by expanding and identifying them and grouping the subpopulations, and determining stem cell factors or tissue lineage potential.

A heterogeneous population of stem cells in the synovial fluid and other tissues, such as blood, cord blood, and fat are identified and are further isolated by methods provided in examples herein. The isolated stem cells are molecularly distinct, small in size, and the different respective subpopulations vary in respective differentiation capacity, and need not express cell surface markers generally associated with other previously identified adult stem cells or with stem cells characterized prior to culture.

Although the ELA cell populations reside in a dormant state in the SF, it is here envisioned that the origin of these stem cells are from the bone marrow and not through systemic circulation. Nakagawa et al. show in a collagen induced arthritis (CIA) model that bone marrow stromal cells migrate directly from the bone marrow in the joint space [Nakagawa, S., et al. J Rheumatol, 1996. 23(12): p. 2098-103]. The enhanced migration of the ELA cell population into the joint space (synovial cavity) increases as result of the inflammations, which accompanies osteoarthritis. These phenomena are known to increase the number and size of bone canals, which communicate between the bone marrow and synovial cavity [Nakagawa et al., supra: Tomita, T., et al. J Rheumatol, 1994. 21(9): p. 1608-14; Marinova-Mutafchieva, L., et al. Arthritis Rheum, 2002. 46(2): p. 507-13]. This increase in bone canal size allows more of the ELA cell population to migrate into the joint space. Under non-inflammatory conditions, these canals are smaller in size and number, thus limiting the number of ELA cells in the joint space.

Phenotypic data indicate that the ELA population possesses the ability to fully differentiate into various tissues. Although the ELA cell population possesses the capacity to differentiate into a specific tissue, the differentiated ELA tissue expresses molecular profiles consistent with that of other tissues (FIG. 3). It is here envisioned that the ELA cell represents an intermediate phenotype and possesses the ability to transdifferentiate into other tissue transfer upon transfer into another specific microenvironment. This finding further supports a concept described by Quensenberry et al. suggesting that expansion, differentiation, and changes in gene expression is continuous and reversible. In particular, the investigators imply that sorting stem cell by positively-selecting static cell surface proteins may eliminate a large percentage of the stem cells and leaving behind a population of cells, which may not truly reflect the total stem cell population [Quesenberry et al., 2007, supra; Quesenberry et al., 2012, supra].

Applying a systems biology approach to adult stem cells results in technologies that are not restricted to a single trait, such as characterized by merely identifying a few cell surface markers. Instead, the properties of the ELA cell including proteomic, genomic, functional (differentiation capacity), epigenetic (microRNA and chromatin methylation), cell networks, canonical pathways, and the cell cycle state are used to understand the biology of the cell and to identify subsets based on these distinctions.

Cellular heterogeneity is not limited to number and types of cell surface markers (phenotype), rather this heterogeneity encompasses functional traits, for example, differentiation, immunosuppression, paracrine factor secretion; and morphology, for example, size and cytoplasm/nucleus ratio. Cells identified and isolated herein are characterized by these parameters. The technologies used herein to isolate, characterize and expand the adult non-embryonic stem cells is herein improved. The newer technologies described in examples herein have resulted in isolation and identification of a heterogenous population of ELA cells which are small in size and in number and in subpopulations derived from the heterogenous population.

Most ASC studies focus on BM-derived stem cells that use discontinuous density gradients, such as Ficoll-Paque and Lymphoprep, and plastic adherence to enrich for ASCs [Insausti, C. L., et al. Stem Cells Dev, 2012. 21(2): p. 260-72]. Although density gradients effectively separate debris, platelets, and red blood cells (RBCs) from the mononuclear cells in the buffy layer, they also inadvertently discard a subset of ASCs [Ratajczak et al., supra]. This technique leads to misleading results in the identification and isolation of progenitor cell populations, as does positive selection because the majority of BM progenitor cells are likely continuously cycling and changing their cell-surface phenotypes [e.g. Quesenberry et al., 2012, supra]. To address population heterogeneity, ASCs should be evaluated on a population basis, not solely by clonal studies.

To avoid potential discrepancies in the isolation of ASCs, methods herein forgo the use of discontinuous gradients and instead use prolonged culture on tissue culture plastic to harvest ASCs. Synovial fluid (SF) was used as a tissue source due to low RBC contamination. To isolate ASCs, time sedimentation of diluted SF was used. Cells in the enriched ASC population measured about 4 μm to about 6 μm in diameter (mean of about 5.9 μm). The original ELA cell population (see U.S. Pat. No. 8,574,567) focused on a physically larger population, from about 6 μm in diameter or larger. Flow cytometry and gene expression analysis indicate small diameter cells in this ASC population express genes and proteins generally thought to be restricted to ESCs. In addition, these small cells did not express MHC class II. CD44, CD45, or CD49 and had minimal MHC class I expression unlike previously described ELA subpopulations which are class I negative. Semi-quantitative PCR studies of the recovered ASCs showed expression of embryonic transcription factors such as Oct4, Rex1, Nanog, and Sox2, indicating pluripotency. The ability of this ASC population, which is referred to herein as ELA cells, to self-renew and differentiate into multiple lineages was investigated. Moreover, the isolation, culture, and expansion conditions were optimized for these cells in vitro. The data herein show that the ELA cells can differentiate into adipose, cartilage, and bone lineages, and that they express genes from other cell types. The stem cells herein are cultured in medium with tissue-specific growth factors, and are expanded both in number and size in these media. Accordingly, the expanded cultured cells are no longer limited to a size range of about 2-8 μm or about 4-6 μm, and instead accumulate size as differentiation proceeds. Cultured cells ultimately achieve a size compatible with fully adult tissues. Further, it is fully recognized that the cultured expanded cells need not express the protein markers of stem cells, and lose one or more of these markers.

The term "adult" as used herein to describe stem cells shall mean non-embryonic and post-natal. It is not limited to any specific age group, and post-natal cells obtained from children are within the scope. It is anticipated that these cells in certain embodiments are homologous to the recipient; accordingly, repair for example of a spinal cord in a child may be achieved with stem cells obtained from synovial fluid of that child.

Further, it was determined that ELA cells are potent modulators of the immune response, potentially by inhibiting T cell proliferation, inducing regulatory CD4+/CD25+ T cells, and inhibiting natural killer (NK) cell activity. Thus like MSCs, the ELA cell population participates in different regenerative processes or work concomitantly in concert with MSCs, to potentially provide new therapies for a wide range of common and orphan diseases.

Current data indicate that MSCs possess immunomodulatory properties [Nauta, A. J. et al. Blood, 2007. 110(10): p. 3499-506; Atoui, R. et al. Stem Cells Transl Med, 2012. 1(3): p. 200.5.] and might play specific roles in the maintenance of peripheral tolerance, transplantation tolerance, autoimmunity, tumor evasion, and fetal-maternal tolerance [Nauta et al. supra]. The application herein describes the role of ELA cells in modulating the immune response by activating T cells. The examples herein show that ELA cells do not induce an allo-immune response, indicating that the ELA cells primarily immunomodulate suppression by affecting the effector arm of the immune response. The in vitro data shown in examples herein indicates that ELA cells suppress T cell activation and induce regulatory T cells. Moreover, ELA cells do not upregulate a surrogate marker of T-cell responsiveness (CD69) in CD3+ T cells [Lindsey, W. B., et al. Cytotherapy, 2007. 9(2): p. 123-3249]. ELA cells might interfere with T cell function in a PD-1 independent pathway [Hikita et al., supra]. PD-1 was observed to be not upregulated in either CD4+ or CD8+ T cells, this does not preclude the possibility that ELA cells secrete factors or express cell surface proteins that modulate T cell function. In addition, ELA cells were shown to inhibit the cytolytic capacity of NK cells. Taken together, these data indicate that ELA cells evade the immune system by interfering with adaptive and innate immunity.

The ELA cell populations are of fundamental importance to the field of regenerative medicine and the development of cell therapeutics. There is an ever-growing need for stem cells that replace, regenerate, and modulate immune function. However, relying on cell and tissue donation is unreliable and cannot address the need for ASCs. Biomanufacturing of ASC therapies is the most logical option [Sherley, J. L., Pharmaceutica Analytica Acta, 2014. 5(2): p. 5]. Although ASCs can be efficiently expanded in the laboratory, this is not easily translated to large-scale production for therapeutic purposes due to technical issues. Therefore, there is a need for cells that can survive prolonged culture periods without affecting the expression of ELA cell-specific genes and ELA cell function.

Embodiments of the invention herein provide populations of cells transformed with a polynucleotide having a sequence encoding Clustered Regularly Interspaced Short Palindromic Repeats (CRISPER) and Cas that uses RNA-guided nucleases to cleave foreign genetic elements. CRISPR systems have been identified across a wide range of bacterial and archaeal hosts, wherein each system includes a cluster of CRISPR-associated (Cas) genes, noncoding RNAs and a distinct array of repetitive elements (direct repeats). These repeats are engineered to be interspaced by short variable sequences obtained from exogenous DNA targets known as protospacers, and together they constitute the CRISPR RNA (crRNA) array. Within the DNA target, each protospacer is associated with a protospacer adjacent motif (PAM), which is specific to the CRISPR system. The examples herein describe using a transgene with the CRISPR-Cas system for allele targeting for repair in cells and tissues carrying deleterious mutations or deleting target polynucleotide sequences from adult cells in the recipient. The methods to transfect CRISPR-Cas system are described in detail in U.S. patent application Ser. No. 14/509,787 filed Oct. 8, 2014 which is hereby incorporated by reference herein in its entirety.

A portion of this work was published as a paper entitled, "Isolation and characterization of early lineage adult stem cells from the synovial fluid of osteoarthritis patients" authored by Shari Benson, Zaheed Hussain, Farnaz Hadaegh, Baldev Vasir, Rudolf Flicker, Katy Goldman and Keith D. Crawford in Jacob's Journal of Regenerative Medicine 2015, 1(1): 005, which paper is incorporated by reference herein in its entirety.

The invention now having been fully described, it is further exemplified by the following examples and claims. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference in their entirety.

EXAMPLES

Example 1: Synovial Fluid (SF) Isolation and Cell Culture

SF was extracted from knees of patients diagnosed with osteoarthritis (OA) following appropriate institutional protocols. Within 24 hours of harvest, the SF was diluted 10:1 in dilution buffer (phosphate-buffered saline (PBS) supplemented with fetal bovine serum (FBS: HyClone, Logan, Utah) and ethylenediaminetetraacetic acid (EDTA; Gibco, Grand Island, N.Y.)). To extract the cellular component, the diluted SF was spun at 500×g for 30 m, and the pellet was resuspended in dilution buffer. This process was repeated twice at 300×g for 30 m, and the final pellet was resuspended in Hank's balanced salt solution (HBSS; Gibco). The pelleted cells were either directly analyzed or subjected to culture expansion and differentiation. Samples that underwent culture expansion and differentiation were suspended in growth medium (MSCGM™ Human Mesenchymal Stein Cell Growth BulletKit™ Medium or MSCGM-CD™ Mesenchymal Stem tableCell Chemically Defined Medium with or without 1% FBS; Lonza) and plated at a concentration of 3000 cells per cm$^2$ (225,000 cells total) in a T-75 vented cell culture flask (BD Biosciences, San Jose, Calif.). All culture media were supplemented with 100 U/ml penicillin and 1000 U/ml streptomycin (PCN-Strep; Gibco) and exchanged every 48 hrs. Once cells reached >80% confluence, they were harvested and replated in new T-75 flasks. Cells were cultured at 37° C. with 5% $CO_2$ for all experiments. Samples were either immediately seeded into cell culture or mixed 1:1 with freezing medium composed of Dulbecco's Modified Eagle's Medium (Gibco) supplemented with 20% FBS and 20% dimethylsulfoxide (Sigma-Aldrich) and stored in liquid nitrogen at −150° C.

Example 2: Flow Cytometric Characterization of ELA Cells

Antibody use was based on the minimal surface marker panel proposed by the International Society of Cellular Therapy [Dominici et al. supra]. Labeled antibodies specific for the following markers and matching isotype controls were obtained from BD Biosciences: CD44-PE, CD45-PE, CD49-PE, CD105-PE, CD133-PE, CD34-PE (clone 581), CD73-PE, CD90-PE, CD99-PE, CD235a-PE, MUC1-PE, HLA Class1-PE, HLA-DR-PE, SSEA1-PE, HLA-DR-PE, IgG1-PE, IgG1-FITC, IgG2a-PE, IgG2bkappa-PE, IgM-PE, CD4-FITC, CD8-FiTC, CD69-PE, CD3-FITC, and CD25-PE. Anti-CXCR4-PE (CD184) antibody was obtained from R&D Systems (Minneapolis, Minn.). Anti-PD1-PE (CD279) antibody was obtained from eBiosciences (San Diego, Calif.). Upon confluence, cells from one 75 cm$^2$ flask were harvested, washed, and counted. Cells were kept on ice and suspended in incubation buffer (Dibco's PBS+2% FBS+1 mM EDTA). After centrifugation and aspiration of supernatant, 5 or 10 µl of antibody (depending on cell number) was applied directly onto the pellet. Cells were incubated at 4° C. for 30-45 minutes, washed, resuspended, and analyzed in a FACSCalibur machine using CellQuest™ software (BD Biosciences). The pluripotent properties and ESC marker status of ELA cells was determined by intracellular staining using monoclonal antibodies against OCTA4-PE, RUNX2-PE, SOX9-PE, REX1-PE, NANOG-PE, and KLF4-PE with matching isotype controls and by RT-PCR of freshly isolated and culture-expanded cells.

Example 3: Self-Renewal Properties of ELA Cells

ELA cells were cultured as monolayers. Positive and negative cultures were set up in parallel. At days three and five, cultures were rinsed with PBS, detached with trypsin-EDTA, centrifuged, and resuspended in media. Duplicate aliquots were placed into 96-well plates, and 10 µl of Cell Counting Kit-8 solution (Dojindo Molecular Technologies Inc., Gaithersburg, Md.) was added to each well. Following a three hour incubation at 37° C., A450 was measured using a Victor5 Light Luminescence Counter (PerkinElmer Life Sciences, Boston, Mass.) and compared with standards of known cell numbers. To detect apoptotic cells, cultures were fixed and stained with the fluorescence-based ApoAlert DNA Fragmentation Assay Kit (BD Biosciences) following the manufacturer's protocol.

Example 4: Adipogenic, Chondrogenic, and Osteogenic Differentiation of Cells Isolated from Synovial Fluid ELA cells were suspended in chemically defined media with 1% FBS, passaged upon reaching 80% confluence, and plated in fibronectin-coated 75 cm$^2$ vented cell culture flasks at a concentration of 150,000/cm$^2$, with a total volume of 25 ml per flask. After 20 passages, cells were plated into fibronectin-coated 12-well plates at a concentration of 200,000 cells/well and cultured in the appropriate differentiation media. For adipogenic differentiation, cells were cultured in StemPro Adipocyte Differentiation Media (Invitrogen) supplemented with PCN-Strep at a total volume of 1.5 nil/well. The media was changed every 48 hours. After 21 days, the cells were harvested for histochemical staining and real-time quantitative PCR (qPCR). Differentiated cells were stained with fresh Oil Red O solution (Sigma-Aldrich) to verify adipocyte characteristics. For chondrogenic differentiation, cells were cultured in Osteocyte/Chondrocyte Differentiation Basal Medium (Invitrogen) with Chondrogenesis Supplement (Invitrogen). The cell cultures were stained with Alcian Blue (Sigma-Aldrich) for chondrocyte detection. For osteogenic differentiation, cells were cultured in Osteocyte/Chondrocyte Differentiation Basal Medium (Invitrogen) with Osteogenesis Supplement (Invitrogen). To assess the presence of osteoblasts, cell cultures were stained with 5-bromo-4-chloro-3-indolyl-phosphate/nitro blue tetrazolium (NBT/BCIP; invitrogen). In three differentiation assays, positive cells were assayed by counting 50-100 cells in multiple fields using light phase microscopy.

Example 5: RNA Isolation and RT-PCR

Total RNA was extracted from freshly isolated and culture-expanded undifferentiated cells and differentiated cells. Total RNA was purified using TRizol® reagent according to the manufacturer's protocol (Invitrogen). The same source of RNA was used for RT-PCR and DNA microarray analysis (see Examples herein). First-strand cDNA was obtained by reverse transcription using 3 mg total RNA according to the manufacturer's instructions (Invitrogen). Primer sequences used in these analyses SEQ ID NOS 1-16 are shown in Table 1. PCR products were electrophoresed on 1.5% agarose gels to verify DNA fragment sizes. For DNA microarray analysis, cDNA was synthesized using the SuperScript™ III First-Strand Synthesis System (Miltenyi Biotec, San Diego, Calif.). RT-PCR assays were performed using qPCR Mastermix Plus for SYBR Green (Miltenyi Biotec) according to the manufacturer's protocol (see Examples herein). For normalization, differential level of gene expression was calculated in relation to beta actin and expressed as a ΔCT value, as previously described in [Antonov et al. supra]. The sequence listing material in computer readable form ASCII text file (3 kilobytes) created Sep. 20, 2016 entitled "29637-047_SequListing.txt", containing sequence listings numbers 1-16, has been electronically filed herewith and is incorporated by reference herein in its entirety.

Example 6: Preparation for DNA Microarray Analysis

Total RNA was extracted from synovial ELA cells in a monolayer culture and aggregates of human synovial ELA cells cultured for 3 days. Cells were lysed using the Super-Amp preparation kit and delivered to Miltenyi Biotec on dry ice. SuperAmp RNA amplification was performed according to Miltenyi Biotec's protocol based on a global PCR protocol. mRNA was isolated using magnetic bead technology. Amplified cDNA samples were quantified using an ND-1000 Spectrophotometer (NanoDrop Technologies), and 250 ng of each cDNA were used as template for Cy3 and Cy5 labeling according to Miltenyi Biotec's protocol. Cy3- and Cy5-labeled cDNAs were combined and hybridized for 17 hours at 65° C. to the Agilent Whole Human Genome Oligo Microarray 4×44 K probe set using Agilent's recommended hybridization chamber and oven. In general, control samples were labeled with Cy3 and experimental samples were labeled with Cy5.

Example 7: Data Processing and Analysis

Feature Extraction Software (Agilent) was used to read and process the microarray image files and raw datasets. These datasets, together with publically available datasets from the NIH Gene Expression Omnibus (GEO), were exported to JMP software (SAS Institute Inc., Cary, N.C.) for further analysis. The input datasets were transformed into log base 2, and row-by-row statistics were computed. Datasets were normalized to the median global intensity.

Example 8: Hierarchical Clustering and Functional Analysis

To identify genes expressed at high levels in ELA cells, an unsupervised hierarchical clustering was performed on the normalized dataset. JMP Software was used to perform and visualize this clustering. One-way ANOVA was performed on the data obtained from the hierarchical clustering, and a volcano plot was generated to represent the intensity ratio each gene in ELA cells and MSCs. The x-axis displays the log 2 ratio of the gene intensities. A log 2 ratio of 1 is approximately a twofold change. The y-axis shows the −log 10 (p-value) for the comparison between ELA cells and MSCs. Genes that were differentially expressed in ELA cells and MSC were identified. These genes, along with their fold-change values, served as the input to the Ingenuity Pathway Analysis (IPA®, Qiagen) program. Differently expressed genes were uploaded into the IPA application and used as the starting point for generating biological networks [Pradines et al. supra]. A right-tailed Fisher's test with $\alpha=0.05$ and the whole database as a reference set were used to determine significance of the enrichment of genes with particular biological functions or molecular processes.

Example 9: Immunomodulatory Properties of ELA Cells

The immunosuppressive properties of ELA cells were assayed by several methods. Suppression of T cell proliferation was determined by in vitro co-culture experiments performed in triplicate. Irradiated and non-irradiated ELA cells, either freshly isolated or cryopreserved and than cultured for 24-48 hours, were co-cultured with freshly isolated human peripheral blood mononuclear cells (PBMCs) at a 1:10 ratio for 5 d at 37° C. ELA cell suppressive function was determined by a [$^3$H]-Thymidine (1 μCi/well; 37 kBq; NEN-DuPont) uptake assay, as previously described in [Vasir, B., et al. J Immunol, 2008. 181(1): p. 808-21]. Data are expressed as counts per minute (cpm) or as a stimulation index (SI). SI was determined by calculating the ratio of experimental [$^3$H]-Thymidine incorporation to background [$^3$H]-Thymidine incorporation by unstimulated T cells. These methods also assessed if ELA cells stimulated allo-reactive T cells, which would be indicated by higher counts in a proliferation assay.

To further demonstrate their immunosuppressive properties, ELA cells were co-cultured with T cells labeled with 5-6-carboxyfluorescein diacetate succinimidyl ester (CFSE; Cell Trace Cell Proliferation Kit; Molecular Probes/Invitrogen Life Technologies) in 96-well plates at 1:10, 1:20, and 1:40 ratios in triplicate, along with non-ELA cell controls. T cell proliferation was stimulated with CD3/CD28 and analyzed with flow cytometry for CFSE fluorescence after 5 days. Immunosuppressive properties of MSCs were assayed in parallel with the same methods. Flow cytometry data was analyzed using FlowJo software (Ashland, Oreg.) to obtain the Proliferation Index (PI). T cell suppression for each sample was calculated as (1−([PI with ELA cells]/[PI without ELA cells])×100. As an additional assay for immunosuppression, freshly isolated ELA cells and PBMCs were co-cultured 1:10 in 96-well plates for 5-7 days, harvested into 5 ml tubes, and labeled with a combination of directly conjugated antibodies as follows: CD4-FITC/CD25-PE; CD8-FITC/CD25-PE; CD3-FITC/CD69-PE, and CD3-FITC/PD1-PE, and matching isotype controls. The percentages of CD4+ or CD8+ T cells expressing CD25+ and CD3+ T cells expressing CD69 or PD1 were determined by bi-dimensional FACS analysis.

ELA cell suppression of NK cell activity was determined by a chromium release assay [Husain, Z., et al. Immunology, 2002. 106(3): p. 373-80]. NK cells were co-cultured with equal numbers of ELA cells in RPMI 1640 tissue culture media (Mediatech, Herndon, Va.) supplemented with 10% pooled human AB serum, antibiotics, and cytokines for 24 h. Following incubation, NK cells were transferred to wells for co-culture with chromium-labeled K562 target cells at 10:1, 5:1, 2.5:1, and 1:1 ratios. Specific cytotoxicity was calculated as 100×(experimental−spontaneous)/(maximum−spontaneous).

Example 10: Statistical Analysis

Results were expressed as mean±SEM. Statistical comparisons were performed using the Student's t-test.

Example 11: Characteristics of SF Mononuclear Cells

Figure 1B:
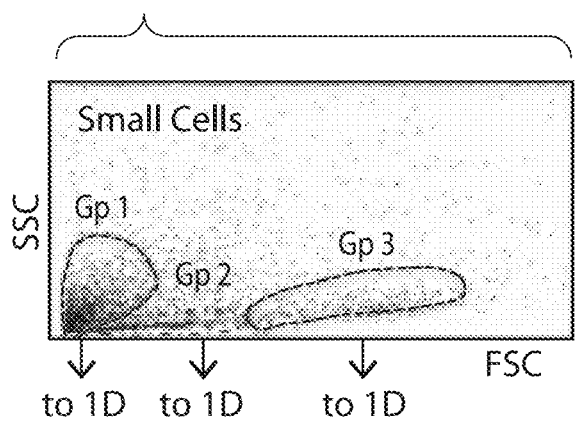
Figure 1C:
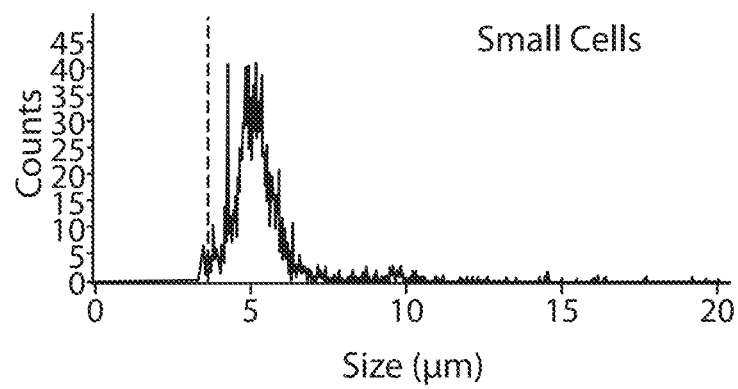

SF contains a wide variety of mononuclear cells, some of which yield a flow cytometry pattern similar to peripheral blood. This pattern consists of four regions, three of which represent neutrophils, myeloid cells, and lymphocytes (FIG. 1A). The fourth region, much smaller in size and side scatter, has previously been thought to primarily represent cell debris and RBCs (FIG. 1B). It was found herein that this population had less fluorescence compared with other regions and <200 forward scatter (FSC) linear units (FIG. 1A). Analysis of this cell population from five OA patients showed a mean viability of 94% (SEM±0.65%) and a mean cell size of 5.9±0.31 μm (range: 4-8 μm) (FIG. 1C) using Roche's CASY Cell Counter and Analyzer System (Roche Applied Sciences).

Figures 1D, 1E:
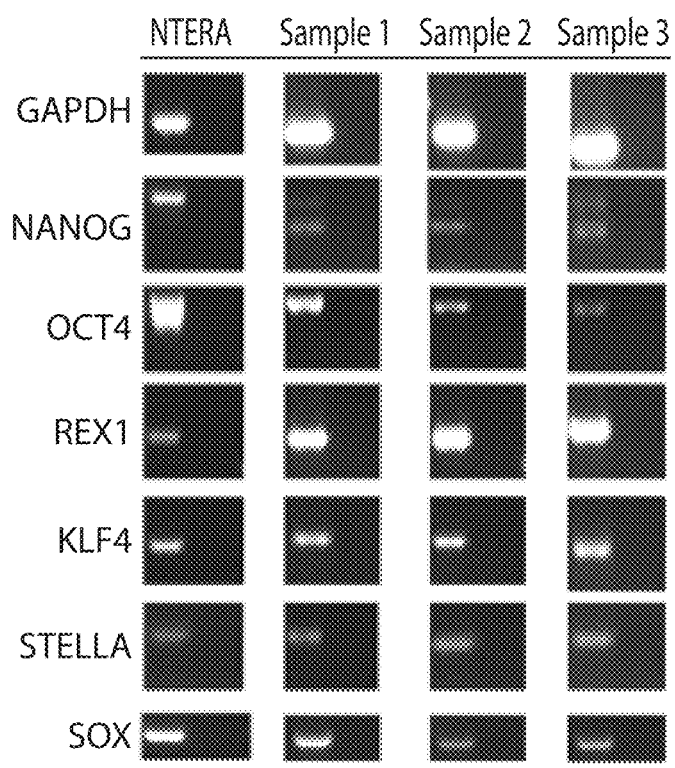

The phenotypic characteristics of these cells were evaluated by staining for proteins associated with peripheral blood mononuclear cells and ASCs. Further flow cytometric analysis showed three distinct subgroups of cells (FIG. 1B). CD45 and CD235a, surface markers of leukocytes and RBCs, respectively, were absent from this cell population. MHC Class I, a protein found on all cells except RBCs and immature stem cells, was observed on a subset of this group (FIG. 1D). Furthermore, very high expression of MUC1 and CD99 was observed in this cell population. Further analysis showed no expression of CD73, CD90, CD105, CD133, CXCR4, or SSEA-1 on any of the subgroups. However, intracellular staining with directly conjugated monoclonal antibodies showed high expression of Rex1 and varying degrees of OCT4, NANOG, SOX9, and RUNX2 expression (FIG. 1D). RT-PCR analysis from three patients revealed that most of the tested pluripotency-associated mRNAs were expressed in this cell population, with REX1 being the most highly expressed (Table 1, FIG. 1E). The Ntera cell line was used as a positive control in these studies [Liu, B., et al. PLoS One, 2014. 9(3): p. e90615].

Example 12: ELA Cell Growth and Self-Renewal

Figure 2A:
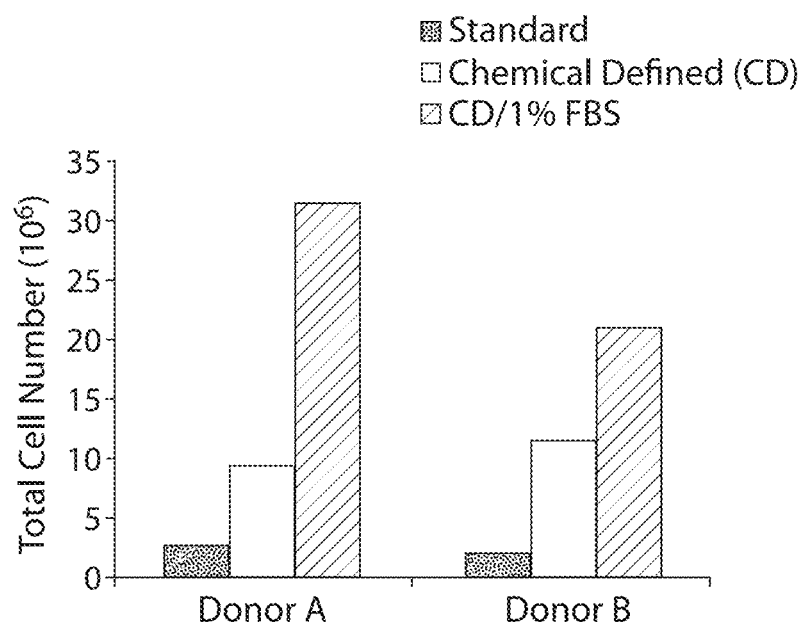
FIG. 2A, FIG. 2B, FIG. 2C and FIG. 2D are bar graphs and micrographs showing cell culture and self-renewal properties of early lineage adult (ELA) cells in vitro.
Figure 2B:
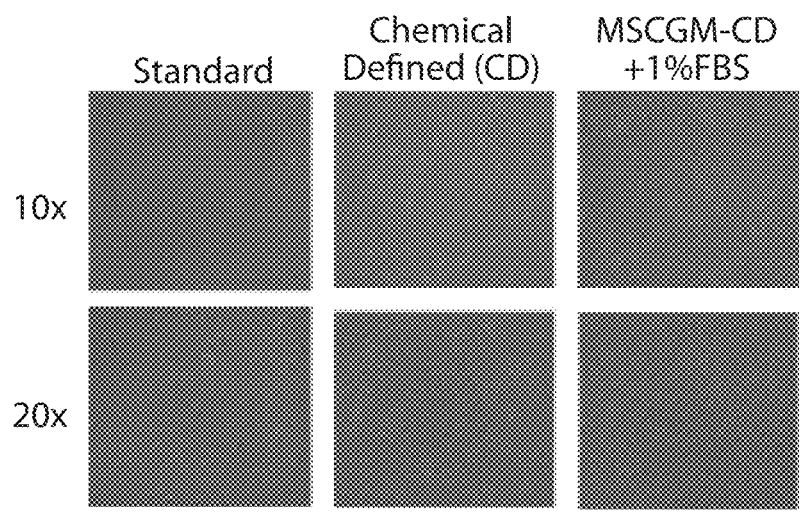
Figure 2C:
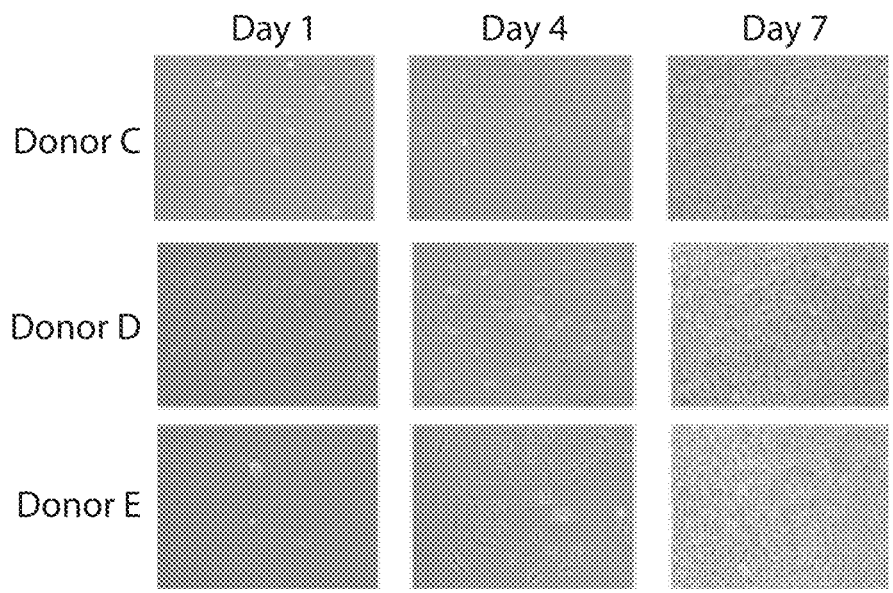
Figure 2D:
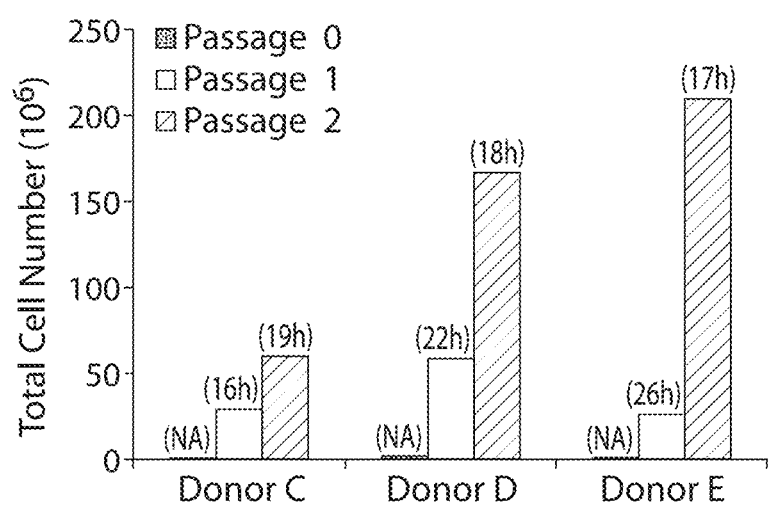

To investigate and optimize cell growth. ELA cells were cultured on fibronectin in four distinct media types: standard expansion medium, chemically defined medium (CD), and CD supplemented with 1% FBS. Cells grown in standard expansion media had an attachment time of seven days and a doubling time of four days, similar to cells grown in CD media. Cells grown in CD media supplemented with 1% FBS had the fastest attachment time (four days) and doubling time (three days); (FIGS. 2A-B). Therefore this culture media was chosen for all future assays. In CD media with 1% FBS media, the morphology of the cells was round immediately after plating but became elongated and spindle-like within 4 days (FIG. 2C). Cells were passaged for up to 20 doublings in fibronectin-coated T-75 flasks with no apparent change in morphology or growth characteristics (FIGS. 2C-D).

Example 13: ELA Cell Differentiation

Figure 3A:
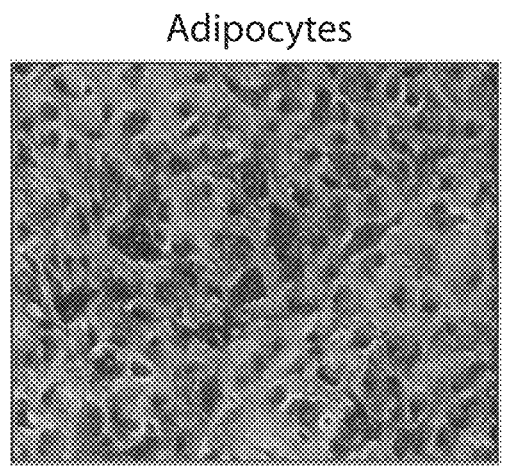
FIG. 3A, FIG. 3B, FIG. 3C, FIG. 3D, FIG. 3E, FIG. 3F are micrographs and bar graphs showing differentiation of early lineage adult (ELA) cells to adipocytes, chondrocytes, and osteocytes. The differentiation potential of ELA cells was investigated by culturing cells for 21 d under conditions that favored adipogenic, chondrogenic, or osteogenic differentiation.
Figure 3B:
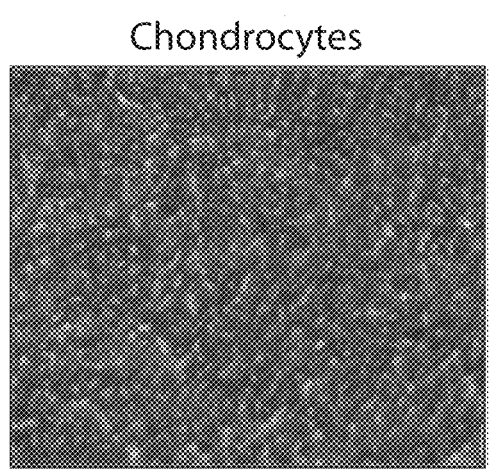
Figure 3C:
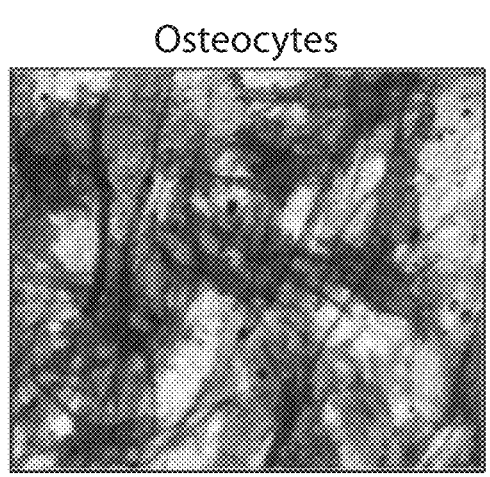

The differentiation potential of ELA cells was investigated by culturing cells under conditions that favored adipogenic, chondrogenic, and osteogenic differentiation. Cells cultured in Adipocyte Differentiation Media for 21 days formed vacuoles that stained positive for Oil Red O, a fat-soluble dye that stains lipids (FIG. 3A). Control cells showed no incorporation of Oil Red O. Cells cultured for 21 days in Chondrocyte Differentiation Media exhibited diffuse Alcian Blue staining, indicating production of acid mucopolysaccharides and glycosaminoglycans normally found in cartilage (FIG. 3B). Cells cultured in Osteocyte Differentiation Media and stained with NBT/BCIP revealed flat, purple cell bodies (FIG. 3C). NBT/BCIP is converted into purple stain by alkaline phosphatase, an enzyme found in osteoblasts. No enzymatic activity was observed in control cells.

TABLE 1

Primer sequences for RT-PCR amplification of target genes

| Gene | Primer | SEQ ID NO: | Gene Bank accession number | Product size (bp) |
|---|---|---|---|---|
| GAPDH | F: 5'-AGCCACATCGCTCAGACAC-3' | 1 | NM_001256799.1 | 66 |
|  | R: 5'-GCCCAATACGACCAAATCC-3' | 2 |  |  |
| NANOG | F: 5'-TGTCTTCTGCTGAGATGCCT-3' | 3 | NM_024865.2 | 88 |
|  | R: 5'-TCTCTGCAGAAGTGGGTTGT-3' | 4 |  |  |
| SOX2 | F: 5'-AGCTCGCAGACCTACATGAA-3' | 5 | NM_003106.3 | 151 |
|  | R: 5'-TGGAGTGGGAGGAAGAGGTA-3' | 6 |  |  |
| OCT4. | F: 5'-ACATGTGTAAGCTGCGGCC-3' | 7 | NM_002701.4 | 297 |
|  | R: 5'-GTTGTGCATAGTCGCTGCTTG-3' | 8 |  |  |
| REX1 | F: 5'-GGATCTCCCACCTTTCCAAG-3' | 9 | NM_020695.3 | 105 |
|  | R: 5'-GCAGGTAGCACACCTCCTG-3' | 10 |  |  |
| GDF3 | F: 5'-TGCTGTTCACTTCAACCTGC-3' | 11 | NM_020634.1 | 156 |
|  | R: 5'-AGGGAGCATCTTAGTCTGGC-3' | 12 |  |  |
| STELLA | F: 5'-GGAAGCTTTACTCCGTCGAG-3' | 13 | NM_199286.3 | 65 |
|  | R: 5'-GCCACTCATCTTCGATTTCC-3' | 14 | (AY230136.1) |  |
| KLF4 | F: 5'-CGTTGACTTTGGGGTTCAGG-3' | 15 | NM_004235.4 | 139 |
|  | R: 5'-GCGAACGTGGAGAAAGATGG-3' | 16 |  |  |

Figure 3D:
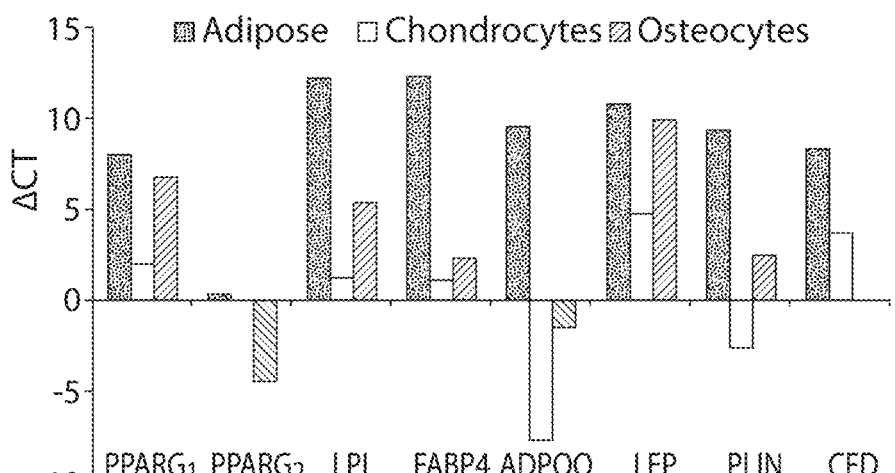
Figure 3E:
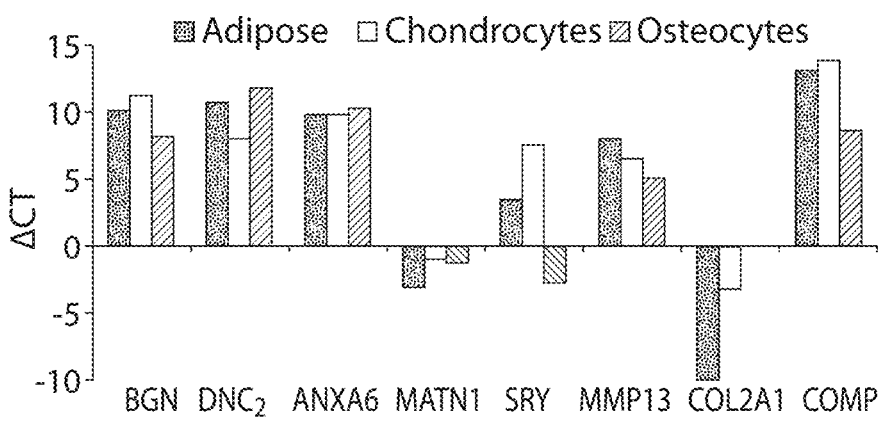
Figure 3F:
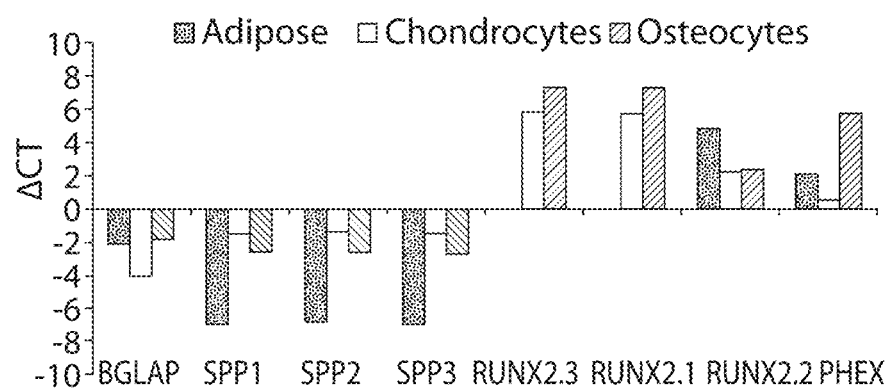

To further investigate the extent of induced ELA cell differentiation, cells were harvested to investigate the presence of adipogenic, chondrogenic, and osteogenic genes by qPCR. Cells from the adipogenesis conditions showed high expression of the adipocyte lineage genes PPARG-tv1, PPARG-tv2, LPL, FABP4, ADIPOQ, LEP, PLIN, and CFD (FIG. 3D). Adipogenesis-specific genes were also detected in chondrogenesis and osteogenesis conditions. Cells from the chondrogenesis conditions showed high expression of the chondrocyte lineage genes BGN, DCN-tvA2, ANXA6-tv2, MMP13, SRY, and COMP and low/absent expression of MATN1 and COL2A1 (FIG. 3E). These genes were also detected at similar levels in cells undergoing adipogenesis or osteogenesis. Cells from the osteogenesis conditions showed high expression of the osteocyte lineage genes RUNX2-tv3, RUNX2-tv1, RUNX2-tv2, and PHEX, similar to the chondrogenesis conditions. RUNX2.2 and PHEX were also detected in adipogenesis conditions. Low/absent expression of BGLAP, SPP1, SPP2, and SPP3 was also observed in the osteogenesis conditions (FIG. 3F). There was low/absent expression of all lineage-specific genes in control cells.

Although cells were cultured in specialized media for differentiation, the differentiation process was not absolute because cells also expressed genes from other lineages (FIGS. 3D-F). To optimize culture conditions for stem cell differentiation, the use of molecular signatures permits definition of the differentiation process. Large-scale gene expression profiling of freshly isolated, undifferentiated ELA cells ex vivo showed expression of differentially expressed progenitor and tissue-specific genes with diverse functions (Table 2). These profiling studies indicated the potential of ELA cells to differentiate into other lineages, such as neuronal, cardiac, pancreatic, and liver cells (Tables 2 and 3). Moreover, the expression of genes with specific cellular functions, such as mucins, ICAM, tetraspans, and collagens (Table 3), indicates that ELA cell differentiation may not be tissue specific. Instead, ELA cells might be a heterogeneous population of multipotent cells with the capacity to differentiate into endodermal, mesodermal, and ectodermal cells.

Table 2 is a list of genes that are expressed at high levels in a pool of fresh uncultured isolated ELA cells. Fluorescent in situ hybridization (FISH) was used to determine whether tissue-specific gene expression is restricted to a single cell or is expressed in a plurality of cells. Table 3 is a list of the genes that express the cell surface proteins. These proteins are used to identify progenitors of the four basic tissue types in the human body: epithelium, connective, muscular, and nervous tissues. Previous characterization has been limited to the use of superficial cell surface markers to identify a possible progenitor cell and subsequent efforts to force that progenitor cell to a particular tissue type. The examples herein identify the functional gene which is capable of expression inside the cell to obtain the progenitor cells from within a heterogenous populations.

Example 14: DNA Microarray Analysis

Figures 4A, 4B:
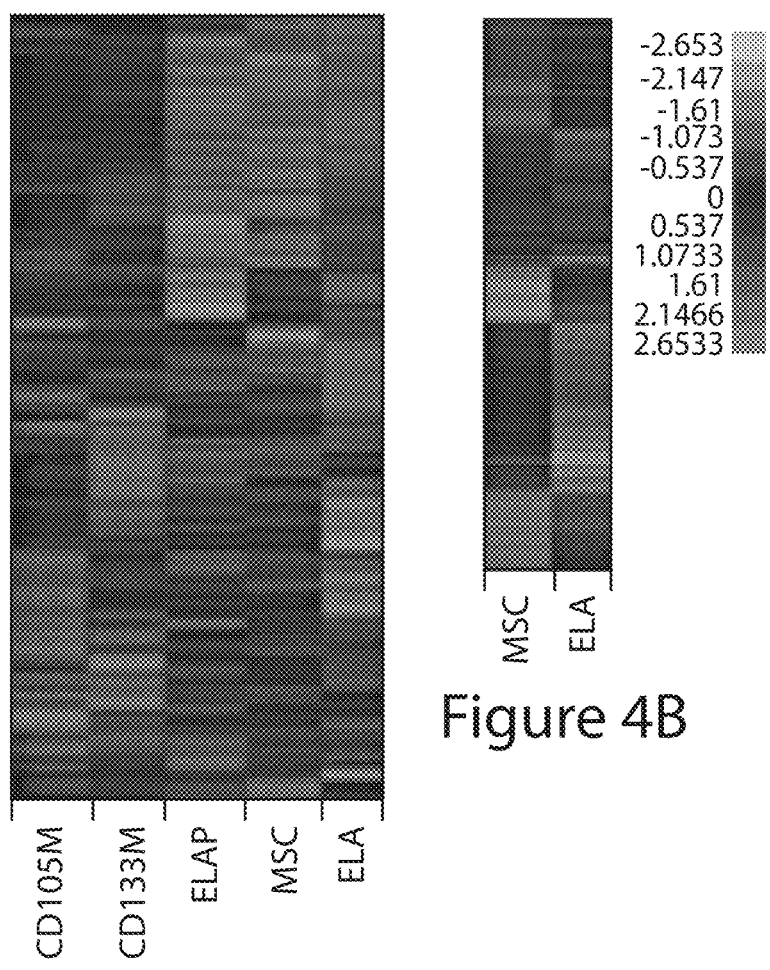
FIG. 4A, FIG. 4B, FIG. 4C, FIG. 4D and FIG. 4E are dendograms, volcano plots, and venn diagrams showing comparison of gene expression profiles of early lineage adult (ELA) cells and mesenchymal stem/progenitor cells (MSCs). Hierarchical cluster analysis of qRT-PCR data was performed on freshly isolated and cultured/expanded ELA cells and bone marrow (BM)-derived, CD105+, and CD133+ MSCs. Expression levels were normalized to β-actin. Colors were used to indicate amounts of expression compared to β-actin. Black was used to represent 1, red was used to represent >1, green was used to represent <1, and grey represented below detection limits.

To compare ELA cells and MSCs, their respective gene expression profiles were examined in triplicates by microarray. The correlation coefficient between these microarray datasets obtained from repeated assays was greater than 0.98, indicating highly reproducibility. The entire set of expressed protein-coding genes was used for a non-supervised hierarchical clustering analysis. The dendrogram in FIG. 4A shows that freshly isolated and frozen/expanded ELA cells isolated from the same tissue were found in different clusters, whereas the three categories of MSCs (BM-derived, CD105+, and CD133+) clustered together. These results indicate that ELA cells have a gene expression profile distinct from MSCs.

Figure 4C:
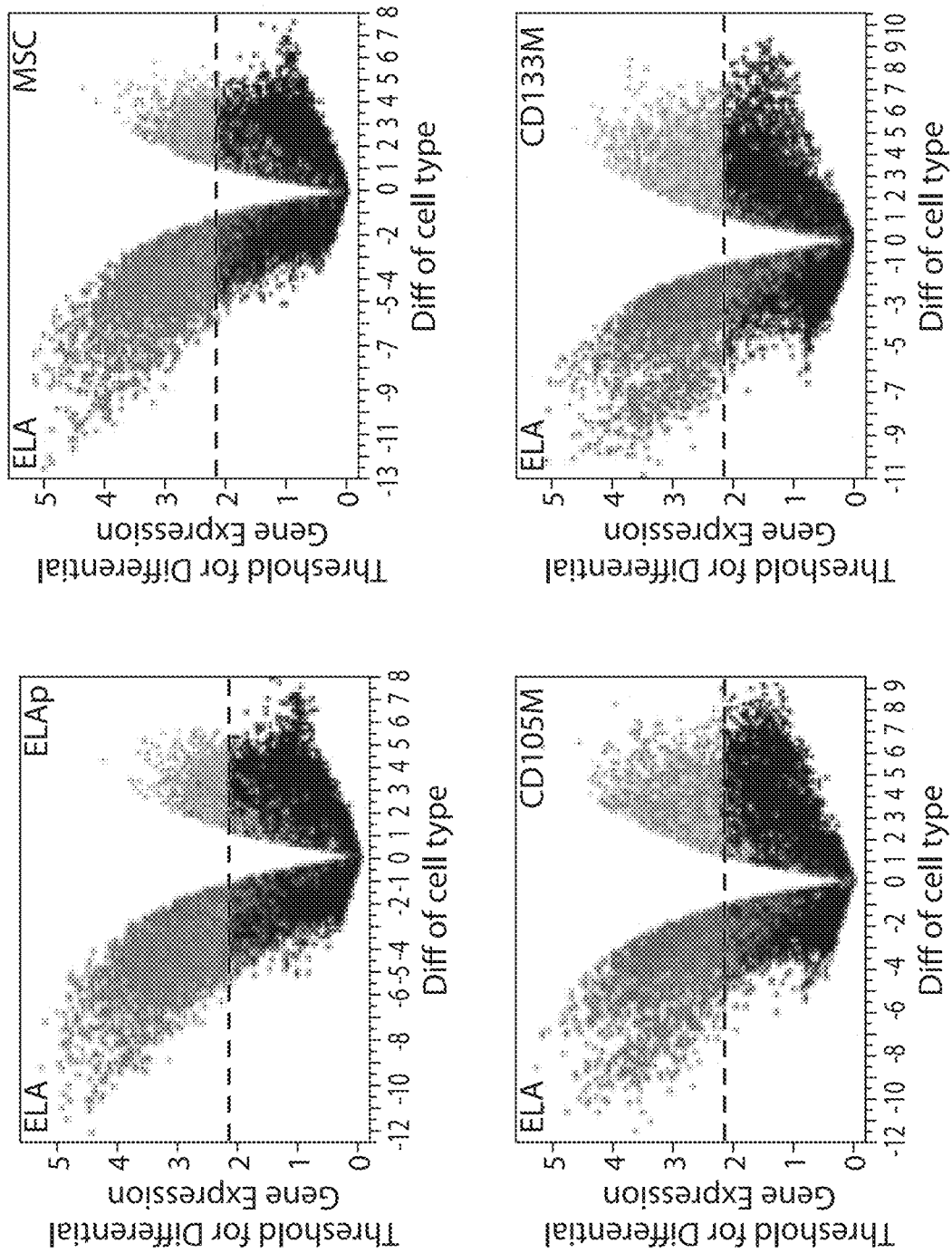
Figure 4D:
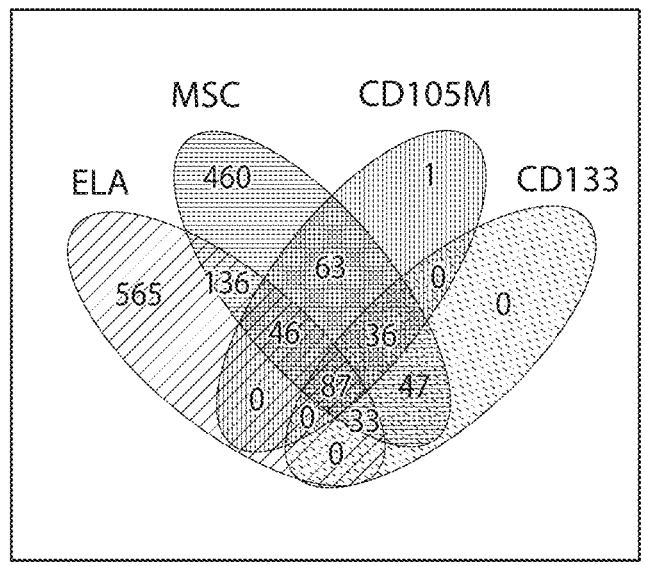
Figure 4E:
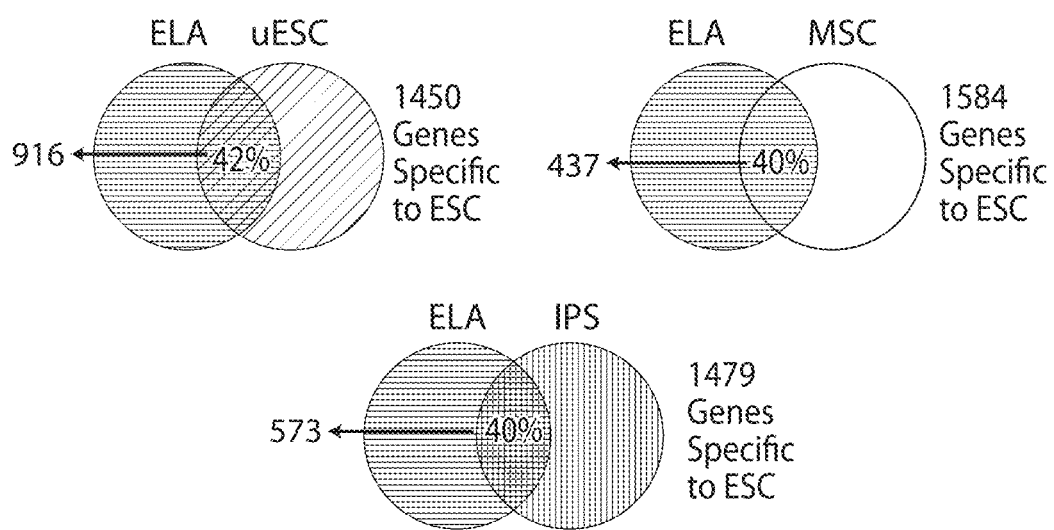

To verify that ELA cells are a distinct population of cells compared with MSCs, high-density oligonucleotide microarrays and functional network analysis were utilized. DNA microarray analysis was used to identify genes expressed in ELA cells, and the results were compared with datasets from the NIH GEO and examples herein (FIG. 4B). This analysis showed that 25% of the genes expressed by ELA cells were shared by BM-derived MSCs (FIG. 4B). The results were visually represented by a volcano plot to compare specific genes upregulated in ELA cells and MSCs (FIG. 4C). Additionally, Venn diagrams were generated to compare gene expression in ELA cells and BM-derived, CD105+, and CD133+ MSCs (FIG. 4D).

Figure 5A:
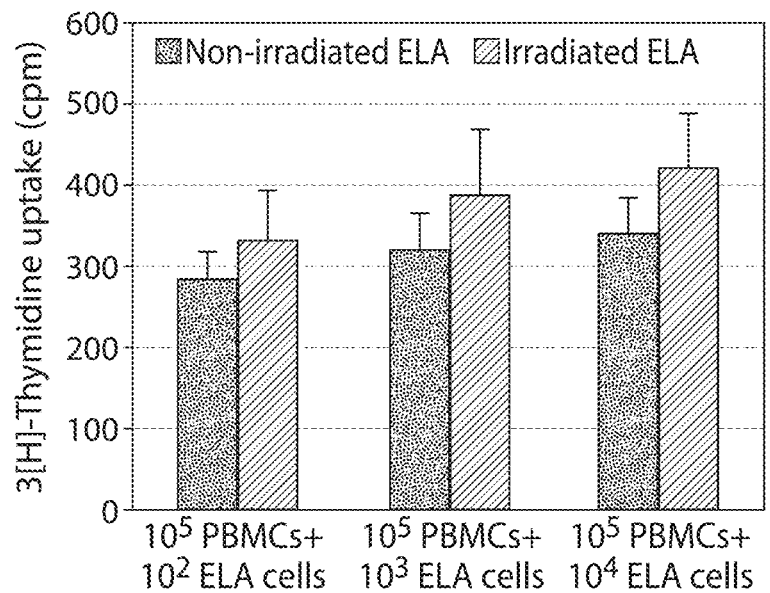
FIG. 5A, FIG. 5B, FIG. 5C, FIG. 5D, FIG. 5E, FIG. 5F and FIG. 5G are bar graphs, scatter graphs and line graphs showing immunomodulatory potential of early lineage adult (ELA) cells.
Figure 5B:
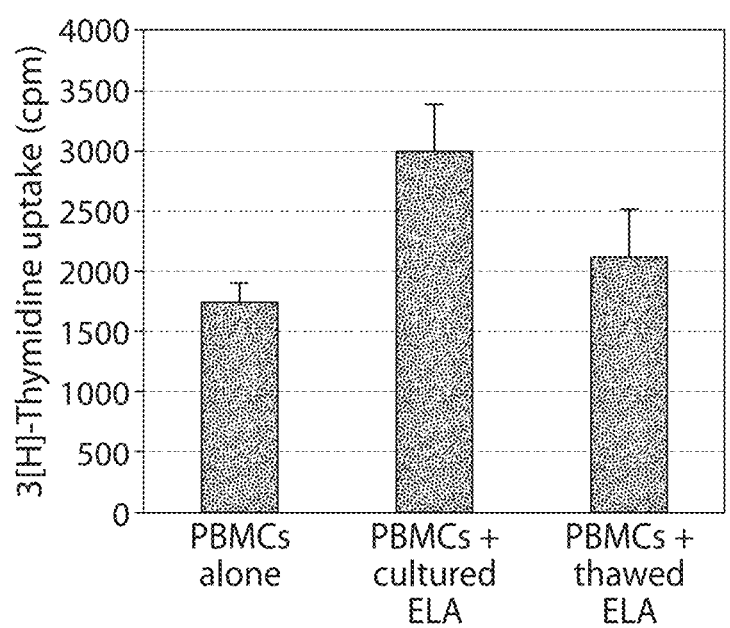
Figure 5C:
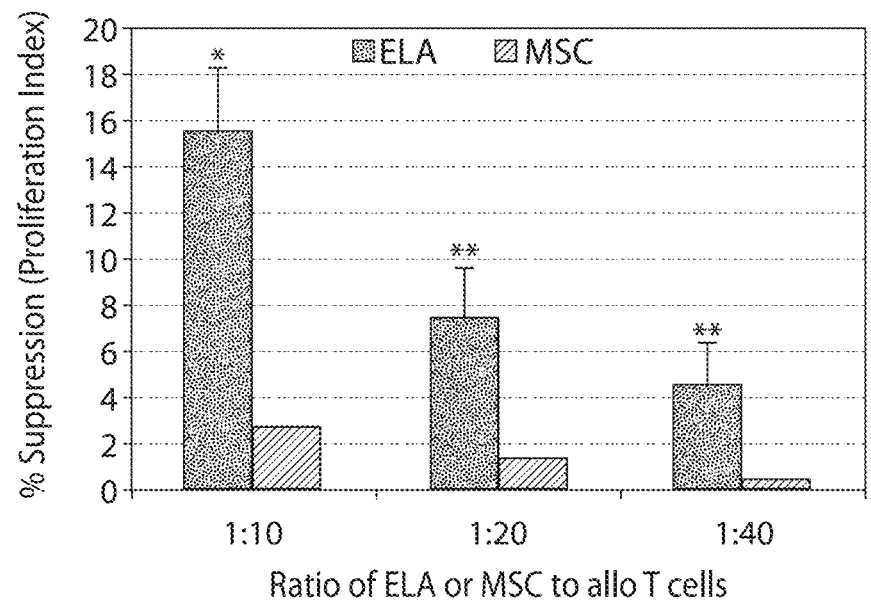
Figure 5D:
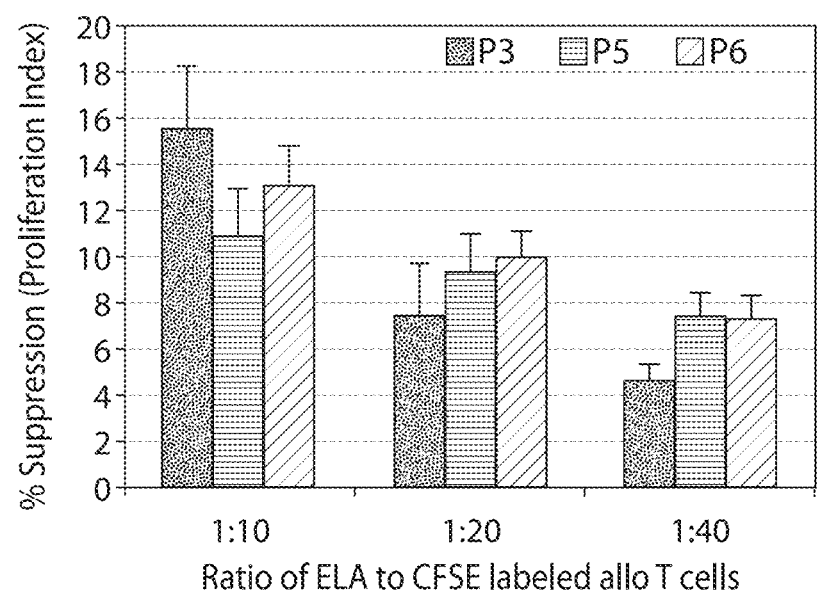
Figure 5E:
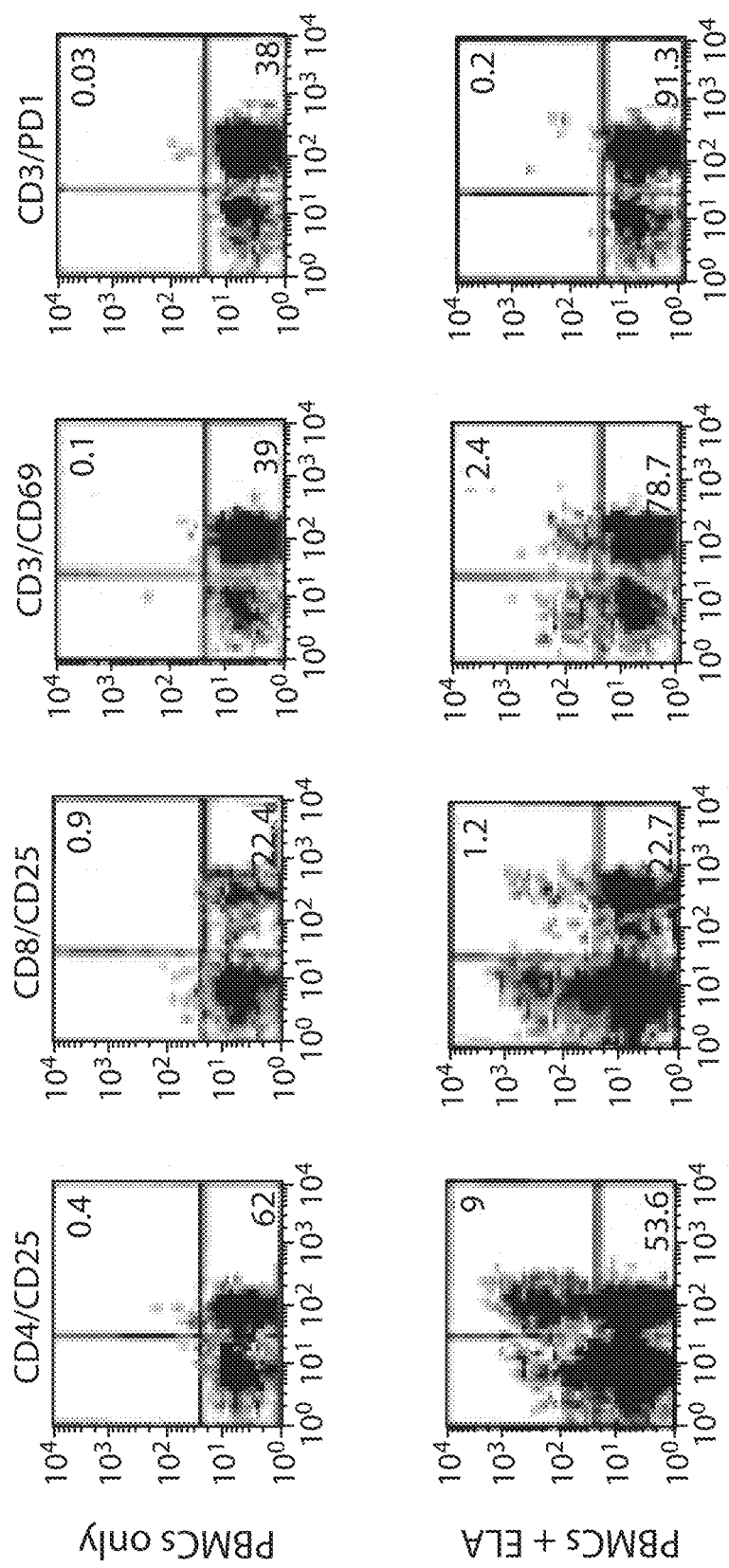

From this analysis, it was concluded that pooled ELA cells represent a distinct population of ASCs. DNA microarray analysis identified genes specific to MSCs, ESCs, and induced pluripotent stem cells (iPSCs) (FIG. 5E). For example, ESCs expressed 1460 genes that were not expressed by the other stem cell types. ELA cells expressed unique genes as well as genes in common with ESCs, MSCs, and iPSCs (Table 4). For example, ELA cells had 616 genes in common with ESCs, signifying a 42% overlap in the genetic profile of the cells. This finding is significant, as these genes play a role in both basic cell functions and functions directly related to stem cell identity, such as self-renewal and pluripotency. Additionally, IPA determined that shared signaling pathways for DNA replication, recombination, and repair were significantly enriched between ELA cells, ESCs and iPSCs (right-tailed Fisher's test, $\alpha=0.05$). Collectively, the data indicates that ELA cells are functional ASCs with a unique set of expressed genes that are not shared with other categories of stem cells.

Table 4 is a list of molecular and cellular functions, physiological system development and function, canonical pathways, and cellular networks. By incorporating this information and old and new data, predictive algorithms are created and used herein to further characterize the ELA population.

Example 15: Immunomodulatory Capacity of ELA Cells

In addition to their regenerative properties, ELA cells possess an immunoregulatory capacity. ELA cells are immune-privileged due to low expression of class II Major Histocompatibility Complex (MHC-II) and c-stimulatory molecules at their cell surfaces (ref) and can interfere with the immune response by cell-to-cell interactions and secretion of soluble factors. The immunosuppressive effects of ELA cells were analyzed by pulsing co-cultures of ELA cells and PBMCs with [$^3$H]-Thymidine for 18 h prior to harvesting. No significant proliferation of allo-reactive T cells was observed. The SI was 1.72±0.19 for fresh ELA cells (n1=3)

and 1.29±0.36 for cryopreserved ELA cells (n=3). Moreover, treatment of ELA cells with the mitogen phytohemagglutinin (PHA) showed no significant proliferation compared with very active proliferation with freshly isolated PBMCs (FIG. 5B). ELA cells at a ratio of 1:10 were shown to elicit a moderate suppressive effect (15.6%±2.7%; n=3) compared to a relatively low suppression by MSCs (2.8%; n=2) on CD3/CD28-stimulated, CFSE-labeled T cells (FIG. 5C). ELA cells at passages three, five and six showed suppression of CD3/CD28-stimulated T lymphocytes, indicating that suppression properties are maintained when ELA cells are expanded in culture, although cells at passage three were most effective (FIG. 5D).

TABLE 2

Selected panel of differentially expressed progenitor- and tissue-specific genes from freshly-isolated ELA cell population

| GENE | NAME | PROGENITOR CELL OR TISSUE |
|---|---|---|
| GABRP | Gamma-Aminobutyric acid A Receptor | Central Nervous System |
| FABP7 | Fatty Acid Binding Protein-7 | Central Nervous System |
| OLIGO-1, -2, -3 | Oligodendrocyte Lineage Transcription | Neuroepithelial progenitor cells within the spinal cord and the telencephalon differentiate into OPC, PMO, and MO. |
| IRX3 | Iroquois homeobox gene family | Neuronal Progenitor Factors |
| TAZ | Tafazzin | Osteochondro Progenitor |
| SOX 10 | SRY (Sex Determining Region- Y)-Box 10 | Osteochondro Progenitor |
| NGN-1 & -3 | Neurogenic Differentiation | Oligodendrocyte Precursor Cells (OPC) are CNS white matter and later develop into (PMO) |
| TCF-4 | Transcription factor 4 | Pre-myelinating Oligodendrocytes (PMO), which mature to become MOC |
| MAG | Myelin Associated Glycoprotein | Myelinating Oligodendrocyte Cells (MOC) that synthesize myelin |
| TSPAN2 | Tetraspan 2 | MOC |
| PTF1A | Pancreas Specific Transcription Factor, 1a | Pancreatic Progenitor |
| PPDPF | Pancreatic Progenitor Cell Differentiation and Proliferation | Pancreatic Progenitor |
| INS | Insulin | Pancreatic tissue |
| GCG | Glucagon | Pancreatic tissue |
| PLA2G12 | Phospholipase A2, Group XIIA | |
| PPY | Pancreatic polypeptide | Pancreatic tissue |
| PNLIP | Pancreatic lipase | Pancreatic tissue |
| CPA-1/2 | Carboxypeptidase A1 | |
| Tm4SF4 | Transmembrane 4 Six Family 4 | Duct progenitor cells |
| Neurod2 | Neuronal Differentiation 2 | Late Immature Amacrine Cells |
| FABPs | Fatty Acid Binding Proteins | Liver |
| TBX3 | Glutaminase 2 | Liver |
| HNF-4A | Hepatocyte Nuclear Factor 4, Alpha | Hepatoblast |
| FOXA2 | Hepatocyte Nuclear Factor 3, Beta | Hepatoblast |
| MET | Mesenchymal epithelial transition factor | Liver and Tissue healing |
| NKX2-5 | Cardiac-specific homeobox | Cardiac Progenitor Cells |
| MEF2C | Myocyte Enhancer Factor 2C | Early Cardiac Myocytes, Cardioblasts |
| FABP3 | Fatty Acid Binding Protein-3 | Muscle, Cardiac and Mammary Growth |
| FABP6 | Fatty Acid Binding Protein-6 | Intestine |
| ACTC1 | Actin, alpha, cardiac muscle 1 | Cardiac muscle |
| TNNT2 | Troponin T type 2 | Cardiac muscle |
| MYL2 | Myosin, light chain 2, regulatory, cardiac, slow | Cardiac muscle |
| MYL7 | Myosin, light chain 7, regulatory | Cardiac muscle |
| MYOZ2 | Myozenin 2 | Cardiac muscle |
| MYH6/7 | Myosin, heavy chain 6, alpha | Cardiac muscle |
| HCN4 | Myosin, heavy chain 7, beta | Cardiac muscle |
| HAND1 | Heart and neural crest derivatives expressed 1 | Cardiac muscle |
| HAND2 | Heart and neural crest derivatives expressed 2 | Cardiac muscle |

Figure 5F:
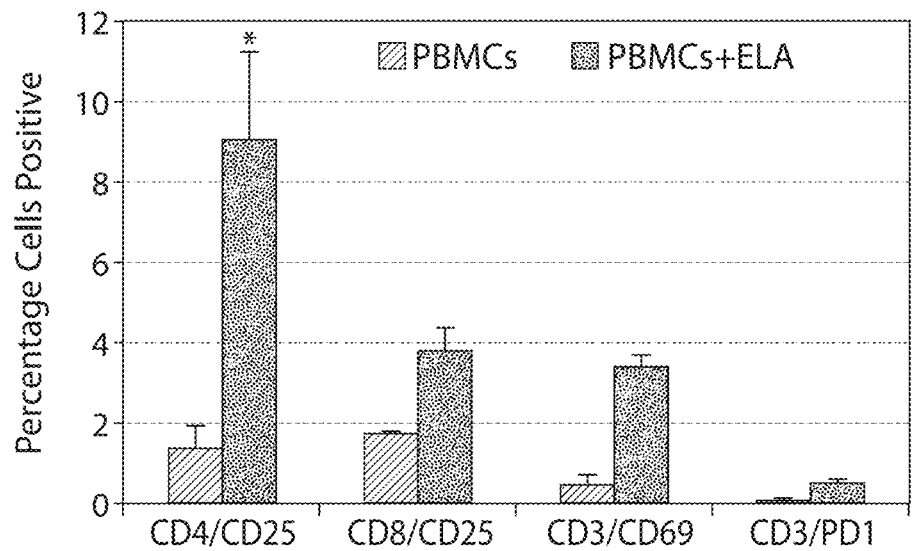

Freshly harvested ELA cells (small population) was isolated from SF of OA patient. Total mRNA from the sample was used for microarray analysis To determine if ELA cells promote the expansion of CD4+/CD25+ regulatory T cells, ELA cells were co-cultured with freshly isolated PBMCs for a period of five days, stained with appropriate antibodies, and analyzed by bi-dimensional FACS analysis. The percentage of CD4+ T cells expressing CD25 expanded three-fold (10%±0.36%; n=3) when co-cultured with ELA cells compared with PBMCs (1.6%±0.36; n=3) (p=0.01) (FIG. 5E-FIG. 5F). The percentage of CD8+ T cells expressing CD25 was 3.6%±0.36% when cultured with ELA cells (n=3), compared to 1.6%±0.36% with PBMCs (n=3). Furthermore, a small population (<1%) of T cells co-cultured with ELA cells expressed PD1 (FIG. 5E-FIG. 5F). PD1 is generally associated with exhaustion of T cells. A modest increase in CD69, a surrogate marker of T-cell responsiveness to mitogen and antigen stimuli was observed in CD3+ T cells cultured with ELA cells (FIG. 5E-FIG. 5F). Taken together, these data indicate that ELA cells perform their immunosuppressive functions by inhibiting T cell proliferation and expanding CD4+ CD25+ regulatory T cells. Accordingly, ELA cells are useful for inducing immunosuppression in situ.

MSCs are known to inhibit the expression of activating receptors on the surface of NK cells and potentially impair their cytotoxic activity.

Figure 5G:
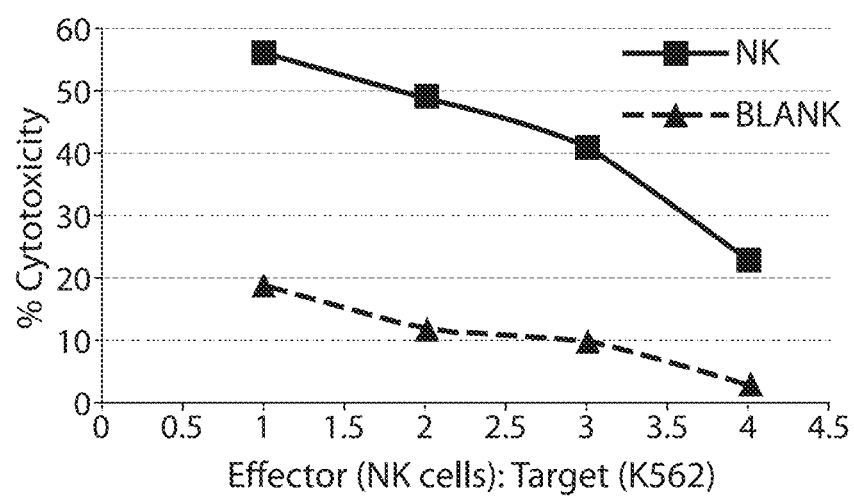

To evaluate potential ELA cell-mediated inhibition of NK cell lytic potential, cytolytic assays were performed. Purified populations of NK cells were co-cultured overnight with and without ELA cells at a 1:1 ratio and than exposed to 51Cr-labeled K562 target cells at various ratios. Cytolytic activity was measured by $^{51}$Cr release. NK cells pre-incubated with ELA cells demonstrated >60% reduction in cytotoxic effects. This reduction was consistent across decreasing concentrations of NK cells (FIG. 5G). These data indicate that ELA cells have a suppressive effect on NK cells.

Example 16: Transfection with CRISPR-Cas System

The ELA cells are transfected by conventional electroporation using a Gene Pulser electroporator (BioRad) at 250 V, 500 uF. Nucleofection is performed using commercial nucleofection kit. Lipofectamine 3000 (Life Technologies, L3000008) and Xfect (Clontech) are used according to manufactures' protocols. To enrich transfected cells, use of medium for a selective marker is performed 48 hours after transfection. Cells are selected in 1.5 µg/ml puromycin at 48 hours post transfection and are used to treat a somatic tissue or organ in the subject.

TABLE 3

Expression of selected group of genes for secreted proteins (collagens/mucins) and surface—expressed proteins (mucins, ICAMS, and tetraspans) in freshly—isolated ELA cells

| Gene | Gene Description | Chr. | Location | Protein Expression |
|---|---|---|---|---|
| COL4A1 | Collagen, type IV, alpha 1 | 13q34 | Secreted | Positive expression in endothelium and in basal membranes of most epithelial tissues |
| COL4A2 | Collagen, type IV, alpha 2 | 13q34 | Secreted | Positive expression in alveolar cells, muscle and stromal cells including, in addition to the small intestine, gall bladder and parts of pancreas. |
| COL8A1 | Collagen, type VIII, alpha 1 | 3q12.1 | Secreted | High level of expression in internal elastic lamina of blood vessels and cytoplasmic and membranous locations premenopausal uterine glands. Connectie tissue, bronchus, renal glomeruli, smooth and skeletal muscles and Langerhans cells also stain positive |
| COL9A2 | Collagen, type IX, alpha 2 | 1q34.2 | Secreted | High expression in gastrointestinal tract, renal tubules and chondrocytes and low expression hepatocytes. |
| COL9A3 | Collagen, type IX, alpha 3 | 20q13.33 | Secreted | Most normal tissues show positive cytoplasmic staining. Glomerular while trophoblastic, and glial cells stain weakly or are negative. |
| COL13A1 | Collagen, type XIII, alpha 1 | 10q22.1 | Secreted | Expressed in breast, trophoblastic cells, salivary gland, seminal vesicle, urothelial cells, pancreatic ducts and squamous epithelial tissue Fallopian tube, gall bladder and bile duct cells were moderate positivity. |
| COL14A1 | Collagen, type XIV, alpha 1 | 8q24.12 | Secreted | Squamous and respiratory epithelia, hepatocytes, urinary and gall bladder, endometrium, Leydig cells gastrointestinal tract and prostate showed moderate. |
| COL15A1 | Collagen, type XV, alpha 1 | 9q22.33 | Secreted | Expressed predominantly in internal organs such as adrenal gland, pancreas and kidney and localized to basement membrane zones, functioning to adhere basement membranes to underlying connective tissue stroma. |
| COL27A1 | Collagen, type XXVII, alpha 1 | 9q32 | Secreted | Involved in the calcification of cartilage and the transition of cartilage to bone |
| MUC1 | Mucin 1, | 1q21 | Cell Surface Associated | Expressed on the apical surface of epithelial cells, especially of airway passages, breast and uterus. |
| MUC2 | Mucin 2 | 11p.15 | Secreted | Expressed in colon, small intestine, colonic tumors, bronchus, cervix and gall bladder. |
| MUC3A | Mucin 3A | 7q22.1 | Cell Surface Associated | Expressed in small intestine, colon, colonic tumors, heart, liver, thymus, prostate, pancreas and gall bladder. |
| MUC4 | Mucin 4 | 3q29 | Cell Surface Associated | Expressed in the thymus, thyroid, lung, trachea, esophagus, stomach, small intestine, colon, testis, prostate, ovary, uterus, placenta, and mammary and salivary glands. |
| MUC5AC | Mucin 5AC | 11p15.5 | Oligomeric Mucus/Gel-Forming | Secreted by gastric and respiratory tract epithelia, which protects the mucosa from infection and chemical damage. |
| MUC6 | Mucin 6 | 11p15.5 | Oligomeric Mucus/Gel-Forming | Expressed in the regenerative zone of gastric antrum, gastric body mucosa and gastric incisura mucosa. |
| MUC7 | Mucin 7 | 4q13.3 | Oligomeric Mucus/Gel-Forming | Expressed in mucous acinar cells of salivary gland tissues and thought to play a role in removal of bacteria in the oral cavity aid in mastication, speech, and swallowing. |
| MUC8 | Mucin 8 | 12q24.33 | Cell Surface Associated | Expressed in the human airway mucin |
| MUC13 | Mucin 13 | 3q21.2 | Cell Surface Associated | Expressed in gastrointestinal and respiratory tracts |
| MUC15 | Mucin 15 | 11p14.2 | Cell Surface Associated | Spleen, thymus, prostate, testis, ovary, small intestine, colon, peripheral blood leukocyte, bone marrow, lymph node and lung |

TABLE 3-continued

Expression of selected group of genes for secreted proteins
(collagens/mucins) and surface—expressed proteins
(mucins, ICAMS, and tetraspans) in freshly—isolated ELA cells

| Gene | Gene Description | Chr. | Location | Protein Expression |
|---|---|---|---|---|
| MUC17 | Mucin 17 | 7q22.1 | Oligomeric Mucus/Gel-Forming | Expressed almost exclusively in the intestine. Encodes a protein that functions as a cytoprotectant, maintains luminal structure, and provide signal transduction |
| MUC19 | Mucin 19 | 12q12 | Oligomeric Mucus/Gel-Forming | Expressed by corneal epithelial cells, mucous cells of the submandibular gland and submucosal gland and trachea middle ear epithelial cells. |
| MUC20 | Mucin 20, Cell Surface Associated | 3q29 | | Expressed kidney, placenta, lung, prostate, liver, and digestive system. |
| ICAM1 | Intercellular Adhesion Molecule 1 (CD54) | 19q13.2 | Cell Surface Associated | Interacts with ntegrins of type CD11a/CD18, or CD11b/CD18 |
| ICAM2 | Intercellular Adhesion Molecule 2 (CD 102) | 17q23.3 | Cell Surface Associated | Interacts with ntegrins of type CD11a/CD18, or CD11b/CD18 |
| ICAM3 | Intercellular Adhesion Molecule 3 (CD50) | 19p13.2 | Cell Surface Associated | Interacts with ntegrins of type CD11a/CD18, or CD11b/CD18 |
| ICAM4 | Intercellular Adhesion Molecule 4 | 19p13.2 | Cell Surface Associated | Landsteiner-Wiener (LW) blood group antigen(s) and that shares similarity with the intercellular adhesion molecule (ICAM) protein family |
| ICAM5 | Intercellular Adhesion Molecule 5, Telencephalin | 19p13.2 | Cell Surface Associated | Expressed in Cerebral cortex, cerebellum, hippocampus, and lateral ventricle, and on the surface of telcephalic neurons and key for neuronal development |
| TSPAN4 | Tetraspanin 4 | 11p15.5 | Cell Surface Associated | Expressed in multiple tissues but is absent in brain, lymphoid cells, and platelets. |
| TSPAN6 | Tetraspanin 6 | Xq22 | Cell Surface Associated | Cytoplasmic and membranous staining was observed in most normal tissues. . |
| TSPAN10 | Tetraspanin 10 | 17q25.3 | Cell Surface Associated | Expressed in the eye including iris, ciliary body, retinal pigment epithelium, but not lens |
| TSPAN14 | Tetraspanin 14 | 10q23.1 | Cell Surface Associated | Expressed in the adrenal gland, Leydig cells, bone marrow, heart, spleen, neurons, skeletal muscle |
| TSPAN15 | Tetraspanin 15 | 10q22.1 | Cell Surface Associated | Expressed in gall bladder, prostate and glandular cells |
| TSPAN16 | Tetraspanin 16 | 19p13.2 | Cell Surface Associated | Expressed in pancreas, bronchus, gall bladder, renal tubules, fallopian tube, Leydig cells, hematopoietic cells and myocytes. |
| TSPAN33 | Tetraspanin 33 | 7q32.1 | Cell Surface Associated | Expressed in pancreas, liver, breast, prostate, and neuronal cells |
| UPK1A (TSPAN21) | Uroplakin 1A | 19q13.12 | Cell Surface Associated | Expressed peripheral nerves, umbrella cells in urothelium, thyroid gland, Purkinje cells, stomach, and adrenal glandular cells. |
| ROM1 | Tetraspanin 23 | 11q12.3 | Cell Surface Associated | Expressed in the photo receptor disk rim of eye |
| CD151 | Tetraspanin 24 (Rod outer segment, membrane protein) | 11p15.5 | Cell Surface Associated | Expressed in blood vessels, and epidermis, but essential for proper assembly of the glomerular and tubular basement membrane of the kidney |

ELA cells were isolated from SF of OA paEents and the total RNA was extracted for microarray analysis. (Chr. Chromosome)

TABLE 4

Common genes expressed in ELA, uESC, IPS, and MSCs together with enriched canonical pathways

| ELA vs. uESC Common Genes | ELA vs. IPS Common Genes | ELA vs. MSC Common Genes |
|---|---|---|
| Top Molecular and Cellular Functions | Top Molecular and Cellular Functions | Top Molecular and Cellular Functions |
| Cell cycle<br>RNA Post-Transcriptional Modification<br>Cell Death<br>DNA replication, Recombination and Repair<br>Cellular Assembly and Organization | DNA replication, Recombination and Repair<br>Cell cycle<br>Cellular Assembly and Organization<br>Cell Death<br>Cellular growth and proliferation | Cellular Movement<br>Cellular Growth and Proliferation<br>Cell Death<br>Cell Morphology<br>Cellular Development |
| Top Physiological System Development and Function | Top Physiological System Development and Function | Top Physiological System Development and Function |
| Connective Tissue Development and Function<br>Cell-Mediated Immune Response<br>Humoral Immune Response<br>Cardiovascular System Development and Function<br>Hepatic System Development and Function | Connective Tissue Development and Function<br>Cell-Mediated Immune Response<br>Humoral Immune Response<br>Organismal survival<br>Tumor Morphology | Organismal Development<br>Tissue Development<br>Cardiovascular System Development and Function<br>Connective Tissue Development and Function<br>Skeletal and Muscular System Development and Function |
| Top Canonical Pathways | Top Canonical Pathways | Top Canonical Pathways |
| Cell Cycle: G2/M DNA Damage Checkpoint Regulation<br>Pyrimidine Metabolism<br>Wnt/B-Catenine Signaling<br>Tight Junction Signaling<br>Role of BRCAI in DNA Damage Response | Parkinson Signaling<br>Tight Junction Signaling<br>Pyrimidine Metabolism<br>Role of BRCAI in DNA Damage Response<br>Cell Cycle: G2/M DNA Damage Checkpoint Regulation | Hepatic Fibrosis/Hepatic Stellate Cell Activation<br>Antigen Presentation Pathway<br>Oncostatin M Signaling<br>IL.6 Signaling<br>TREMI Signaling |
| Top Networks | Top Networks | Top Networks |
| Cell Death, Cancer, Cellular Movement<br>DNA Replication, Recombination, and Repair, Cell Cycle, Cancer Gene Expression, Cell Cycle, and Cancer<br>Cell Cycle, Cancer, Cellular Growth and Proliferation | DNA Replication, Recombination, and Repair, Cell Cycle, Cancer<br>DNA Replication, Recombination, and Repair, Cell Cycle, Cancer<br>DNA Replication, Recombination, and Repair, Cell Cycle, Cellular Assembly and Organization<br>Cellular Assembly and Organization, RNA Post. Transcriptional Modification, Cardiovascula Disease<br>Gene Expression, Cell Cycle, Dermatological disease and condition | Infection Mechanism, Cancer, Gene Expression<br>Cellular Movement, Cancer, Cell-to-Cell Signaling and Interaction.<br>Cellular Growth and Proliferation, Cancer, Cell Cycle<br>Gene Expression, Cell Death, Tissue development a Gene Expression, Developmental Disorder, Genetic-Disorder |

Genes expressed in ELA cells were compared with publicly available datasets from the NIH Gene Expression Omnibus: The Ingenuity Pathway Analysis (IPA) was used for identifying canonical pathways that were significantly enriched (Right-tailed Fisher test with a = 0.05)

What is claimed is:

1. A population of isolated human progenitor cells, comprising: a plurality of cells having diameters ranging from about 2 µm to about 8 µm, which express one or more of stem cell associated genes Oct-4, KLF-4, Nanog, Sox-2, Rex-1, GDF-3 or Stella, and are CD99+ or a MUC-1+ isoform; and further express one or more of a tetraspan, an ICAM, CD13, CD45, CD105, CD133, MHC class I or MHC class II; but do not detectably express surface antigens CD34, CD44, CD73, CD90, CXCR4 or SSEA-4; and the cells comprise a recombinant polynucleotide.

2. The population of isolated human progenitor cells according to claim 1, wherein the cells express at least one of Oct-4, KLF-4, Nanog, Sox-2, Rex-1, GDF-3, and Stella, and is CD 13+ but do not detectibly express, CD34, and CD90.

3. The population of isolated human progenitor cells according to claim 1, wherein the cells express at least one of Oct-4, KLF-4, Nanog, Sox-2, Rex-1, GDF-3, and Stella, and do not detectibly express CD34, CD90, and is MHC class I+.

4. The population of isolated human progenitor cells according to claim 1, wherein the cells express at least one of Oct-4, KLF-4, Nanog, Sox-2, Rex-1, GDF-3, and Stella, and do not detectibly express CD34, CD90, but are MHC class I+ and CD105+.

5. The population of isolated human progenitor cells according to claim 1, wherein the cells express at least one of Oct-4, KLF-4, Nanog, Sox-2, Rex-1, GDF-3, and Stella, and do not detectibly express CD34, CD90, and is CD105+.

6. The population of isolated human progenitor cells according to claim 1, the cells are expanded and induced for mesodermal lineage differentiation.

7. The population of isolated human progenitor cells according to claim 1, the cells are expanded and induced for endodermal lineage differentiation.

8. The population of isolated human progenitor cells according to claim 1, the cells are expanded and induced for ectodermal lineage differentiation.

9. The stem cells according to claim 1, wherein the recombinant polynucleotide encodes a transgene.

10. The stem cells according to claim 9, wherein the transgene further comprises at least one of: a nucleotide sequence encoding a CRISPR system component and a gene encoding a Cas protein.

11. The stem cells according to claim 1, wherein the isolated human adult stem cells are at least about 4 μm to about 6 μm in diameter.

12. The stem cells according to claim 3, wherein the isolated human adult stem cells have a mean diameter of about 5.9 μm.

13. The stem cells according to claim 3, wherein the isolated human adult stem cells have a diameter greater than about 6 μm and are MHC class I+.

* * * * *

SEQUENCE LISTING

```
<160> NUMBER OF SEQ ID NOS: 16

<210> SEQ ID NO 1
<211> LENGTH: 19
<212> TYPE: DNA
<213> ORGANISM: Homo sapiens

<400> SEQUENCE: 1
agccacatcg ctcagacac                                              19

<210> SEQ ID NO 2
<211> LENGTH: 19
<212> TYPE: DNA
<213> ORGANISM: Homo sapiens

<400> SEQUENCE: 2
gcccaatacg accaaatcc                                              19

<210> SEQ ID NO 3
<211> LENGTH: 20
<212> TYPE: DNA
<213> ORGANISM: Homo sapiens
```

```
<400> SEQUENCE: 3
tgtcttctgc tgagatgcct                                              20

<210> SEQ ID NO 4
<211> LENGTH: 20
<212> TYPE: DNA
<213> ORGANISM: Homo sapiens

<400> SEQUENCE: 4
tctctgcaga agtgggttgt                                              20

<210> SEQ ID NO 5
<211> LENGTH: 20
<212> TYPE: DNA
<213> ORGANISM: Homo sapiens

<400> SEQUENCE: 5
agctcgcaga cctacatgaa                                              20

<210> SEQ ID NO 6
<211> LENGTH: 20
<212> TYPE: DNA
<213> ORGANISM: Homo sapiens

<400> SEQUENCE: 6
tggagtggga ggaagaggta                                              20

<210> SEQ ID NO 7
<211> LENGTH: 19
<212> TYPE: DNA
<213> ORGANISM: Homo sapiens

<400> SEQUENCE: 7
acatgtgtaa gctgcggcc                                               19

<210> SEQ ID NO 8
<211> LENGTH: 21
<212> TYPE: DNA
<213> ORGANISM: Homo sapiens

<400> SEQUENCE: 8
gttgtgcata gtcgctgctt g                                            21

<210> SEQ ID NO 9
<211> LENGTH: 20
<212> TYPE: DNA
<213> ORGANISM: Homo sapiens

<400> SEQUENCE: 9
ggatctccca cctttccaag                                              20

<210> SEQ ID NO 10
<211> LENGTH: 19
<212> TYPE: DNA
<213> ORGANISM: Homo sapiens

<400> SEQUENCE: 10
gcaggtagca cacctcctg                                               19

<210> SEQ ID NO 11
<211> LENGTH: 20
<212> TYPE: DNA
```

```
<213> ORGANISM: Homo sapiens

<400> SEQUENCE: 11
tgctgttcac ttcaacctgc                                               20

<210> SEQ ID NO 12
<211> LENGTH: 20
<212> TYPE: DNA
<213> ORGANISM: Homo sapiens

<400> SEQUENCE: 12
agggagcatc ttagtctggc                                               20

<210> SEQ ID NO 13
<211> LENGTH: 20
<212> TYPE: DNA
<213> ORGANISM: Homo sapiens

<400> SEQUENCE: 13
ggaagcttta ctccgtcgag                                               20

<210> SEQ ID NO 14
<211> LENGTH: 20
<212> TYPE: DNA
<213> ORGANISM: Homo sapiens

<400> SEQUENCE: 14
gccactcatc ttcgatttcc                                               20

<210> SEQ ID NO 15
<211> LENGTH: 20
<212> TYPE: DNA
<213> ORGANISM: Homo sapiens

<400> SEQUENCE: 15
cgttgacttt ggggttcagg                                               20

<210> SEQ ID NO 16
<211> LENGTH: 20
<212> TYPE: DNA
<213> ORGANISM: Homo sapiens

<400> SEQUENCE: 16
gcgaacgtgg agaaagatgg                                               20
```